(12) United States Patent
Lee et al.

(10) Patent No.: US 12,410,281 B2
(45) Date of Patent: Sep. 9, 2025

(54) DIAMINE COMPOUND, POLYIMIDE PRECURSOR AND POLYIMIDE FILM USING THE SAME, AND USE THEREOF

(71) Applicants: SK Innovation Co., Ltd., Seoul (KR); SK ie technology Co., Ltd., Seoul (KR)

(72) Inventors: Joo Hyun Lee, Daejeon (KR); Sang Yoon Park, Daejeon (KR); So Young Lee, Daejeon (KR)

(73) Assignees: SK Innovation Co., Ltd., Seoul (KR); SK ie technology Co., Ltd., Seoul (KR)

( * ) Notice: Subject to any disclaimer, the term of this patent is extended or adjusted under 35 U.S.C. 154(b) by 746 days.

(21) Appl. No.: 17/735,811

(22) Filed: May 3, 2022

(65) Prior Publication Data

US 2022/0389165 A1 Dec. 8, 2022

(30) Foreign Application Priority Data

May 4, 2021 (KR) .......................... 10-2021-0057925
Apr. 4, 2022 (KR) .......................... 10-2022-0041615

(51) Int. Cl.
*C07D 241/04* (2006.01)
*C07D 295/16* (2006.01)
*C07D 498/08* (2006.01)
*C08G 73/10* (2006.01)
*C08J 5/18* (2006.01)

(52) U.S. Cl.
CPC ....... *C08G 73/1007* (2013.01); *C07D 295/16* (2013.01); *C07D 498/08* (2013.01); *C08G 73/1067* (2013.01); *C08J 5/18* (2013.01); *C08J 2379/08* (2013.01)

(58) Field of Classification Search
CPC .. C07D 241/04; C07D 243/08; C07D 401/10; C07D 473/16
See application file for complete search history.

(56) References Cited

U.S. PATENT DOCUMENTS

2010/0160626 A1 6/2010 Anderson et al.
2019/0292138 A1 9/2019 Yun et al.

FOREIGN PATENT DOCUMENTS

| JP | 2013136575 A | 7/2013 | |
|---|---|---|---|
| KR | 1020080017410 A | 2/2008 | |
| KR | 1020190102299 A | 9/2019 | |
| WO | 9837077 A1 | 8/1998 | |
| WO | WO-2019031604 A1 * | 2/2019 | ............. C08G 73/10 |

* cited by examiner

*Primary Examiner* — Gregory Listvoyb
(74) *Attorney, Agent, or Firm* — The Webb Law Firm

(57) ABSTRACT

Provided a diamine compound, a polyimide precursor and a polyimide film using the same, and a use thereof. The diamine compound may be very useful as a monomer for manufacturing a polyimide film having excellent transparency, high heat resistance, and low retardation.

8 Claims, No Drawings

DIAMINE COMPOUND, POLYIMIDE PRECURSOR AND POLYIMIDE FILM USING THE SAME, AND USE THEREOF

CROSS-REFERENCE TO RELATED APPLICATIONS

This application claims priority to Korean Patent Application No. 10-2021-0057925 filed May 4, 2021, and Korean Patent Application No. 10-2022-0041615 filed Apr. 4, 2022, the disclosures of which are hereby incorporated by reference in their entirety.

BACKGROUND OF THE INVENTION

Field of the Invention

The following disclosure relates to a diamine compound, a method of preparing the same, and a composition including the same, and more particularly, to a diamine compound which is a monomer useful for manufacture of a polyimide film, a method of preparing the same, and a composition including the same.

In addition, the following disclosure relates to a polyimide precursor prepared from the diamine compound, a polyimide precursor composition, a polyimide film, a method of manufacturing the same, and a use thereof.

Description of Related Art

Polyimide (PI) is conceived as a material which has high heat resistance and is also light and soft. Polyimide is a polymer which has a relatively low crystallinity or mostly has a non-crystalline structure, and is a polymer material having advantages of being easily synthesized, being produced into a thin film, and not needing a crosslinking group for curing, and also having excellent heat resistance, chemical resistance, mechanical properties, electrical properties, and dimensional stability due to a rigid chain structure, and currently, is widely used as electrical or electronic materials of an automobile, an aerospace field, a flexible circuit substrate, a liquid crystal alignment film for LCD, adhesive and coating agents, and the like.

In the fields of polyimide as such, an aromatic polyimide is receiving attention as a resin having excellent thermal dimensional stability. A polyimide film which is a molded body formed of an aromatic polyimide of which the chemical structure is rigid and straight is widely used in the fields requiring high thermal dimensional stability (low coefficient of linear thermal expansion), such as a base film of a flexible substrate or an interlayer insulating film of a semiconductor. However, since an aromatic polyimide having a low coefficient of linear thermal expansion is strongly colored by conjugation in molecules and a charge transfer interaction in/between molecules, it is difficult to apply the aromatic polyimide to an optical use. In addition, since a polyimide has a very strong intermolecular force, it lacks processability.

Meanwhile, a flexible device is manufactured by a method of applying a polyimide precursor composition on a conveyance board and curing the composition to form a film, completing a device by a subsequent process such as deposition of a thin film transistor (TFT) and an organic film, and then desorbing the completed device from the conveyance board. As such, the flexible device involving a high temperature process requires heat resistance at a high temperature. In particular, when a thin film transistor process using low temperature polysilicon (LIPS) is used, the process temperature may approach 500° C., and thus, a polyimide film formed on the conveyance board does not undergo thermal decomposition by hydrolysis even during the high temperature process and should satisfy high heat resistance. In addition, transparency after processing as well as storage stability should be secured.

In addition, when a polyimide resin material is used as a substrate of a display, it is preferred that the resin material has excellent transparency and a low retardation. Retardation means a product of birefringence (difference in two orthogonal refractive indices) and a film thickness, and in particular, the retardation in the thickness direction is an important value affecting viewing angle properties. Since a high retardation value may cause deterioration of display quality of a display, low retardation value properties are required for the flexible display substrate, in addition to high flexibility.

Thus, a polyimide which may implement both stable optical properties and excellent heat resistant properties is required, in order to manufacture a flexible device. The physical properties of the polyimide are derived from a monomer for preparing polyimide, and thus, in order to prepare a polyimide having more improved physical properties, development of a monomer is needed.

RELATED ART DOCUMENTS

Patent Documents (Patent Document 1) US 2019-0292138 A1 (Sep. 26, 2019)

SUMMARY OF THE INVENTION

An embodiment of the present invention is directed to providing a diamine compound having a structure which is very useful as a monomer to be manufactured into a highly transparent polyimide film having improved physical properties, in particular, retardation improvement properties, and a method of preparing the same.

Another embodiment of the present invention is directed to providing a polyimide-based polymer composition including the diamine compound.

Another embodiment of the present invention is directed to providing a polyimide precursor for manufacturing a polyimide film having improved physical properties using the diamine compound.

Another embodiment of the present invention is directed to providing a low-retardation and highly transparent polyimide film using the polyimide precursor.

Still another embodiment of the present invention is directed to providing a laminate and a photoelectric device including the polyimide film.

In one general aspect, a diamine compound having a structure, which is useful as a monomer of a polyimide precursor for manufacturing a polyimide film having improved physical properties, in particular, retardation improvement properties, is provided, and the diamine compound is represented by the following Chemical Formula 1:

[Chemical Formula 1]

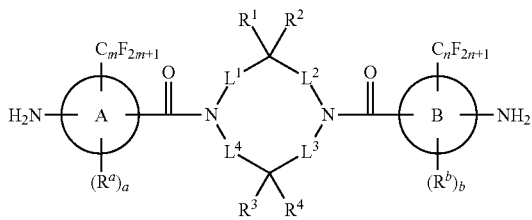

wherein
$L^1$ to $L^4$ are independently of one another a single bond or C1-C10 alkylene;
$R^1$ to $R^4$ are independently of one another hydrogen, halogen, C1-C10 alkyl, haloC1-C10 alkyl, C1-C10 alkoxy, C3-C10 cycloalkyl, or C6-C20 aryl, or $R^1$ and $R^3$ may be linked to each other by —NR'—, —O—, or —S— to form a ring;
R' is hydrogen, C1-C10 alkyl, C3-C10 cycloalkyl, or C6-C20 aryl,
ring A and ring B are independently of each other a C6-C20 aromatic ring;
$R^a$ and $R^b$ are independently of each other halogen, C1-C10 alkyl, haloC1-C10 alkyl, C1-C10 alkoxy, C3-C10 cycloalkyl, or C6-C20 aryl;
a and b are independently of each other an integer of 0 to 3; and
m and n are independently of each other an integer of 1 to 10.

According to an exemplary embodiment, $L^1$ and $L^3$ may be independently of each other a single bond or C1-C5 alkylene; $L^2$ and $L^4$ may be independently of each other C1-C5 alkylene; and ring A and ring B may be independently of each other benzene or naphthalene.

According to an exemplary embodiment, the diamine compound of Chemical Formula 1 may be represented by the following Chemical Formula 2 or 3:

[Chemical Formula 2]

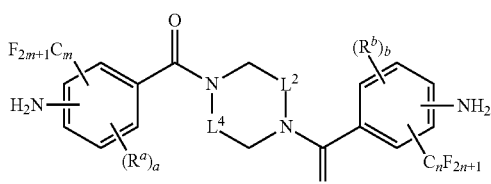

[Chemical Formula 3]

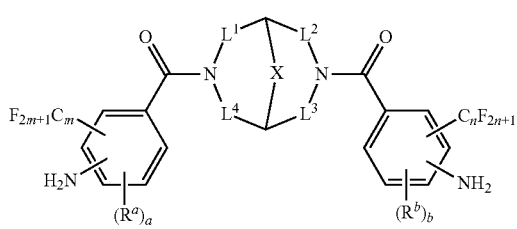

wherein
$L^1$ to $L^4$ are independently of one another C1-C5 alkylene;
X is —NR'—, —O—, or —S—;
R' is hydrogen or C1-C5 alkyl;
$R^a$ and $R^b$ are independently of each other halogen, C1-C5 alkyl, haloC1-C5 alkyl, C1-C5 alkoxy, C3-C7 cycloalkyl, or C6-C12 aryl;

a and b are independently of each other an integer of 0 or 1; and
m and n are independently of each other an integer of 1 to 5.

According to an exemplary embodiment, the diamine compound of Chemical Formula 2 may be represented by the following Chemical Formula 4:

[Chemical Formula 4]

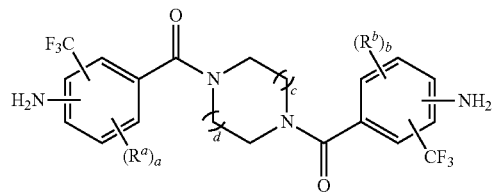

wherein
$R^a$ and $R^b$ are independently of each other halogen, C1-C5 alkyl, or haloC1-C5 alkyl;
a and b are independently of each other an integer of 0 or 1; and
c and d are independently of each other an integer of 1 or 2.

According to an exemplary embodiment, the diamine compound of Chemical Formula 3 may be represented by the following Chemical Formula 5:

[Chemical Formula 5]

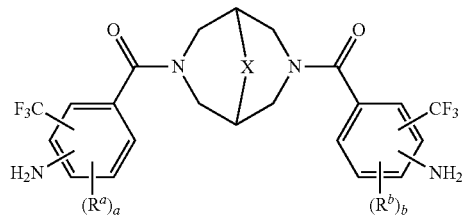

wherein
X is —O— or —S—;
$R^a$ and $R^b$ are independently of each other halogen, C1-C5 alkyl, or haloC1-C5 alkyl; and
a and b are independently of each other an integer of 0 or 1.

The diamine compound according to an exemplary embodiment may be selected from the following, but is not limited thereto:

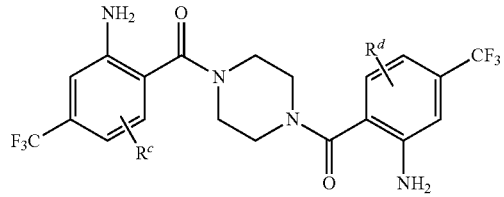

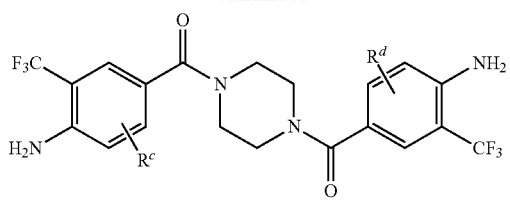
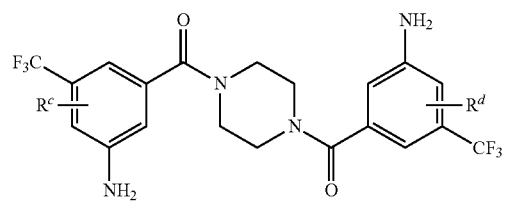
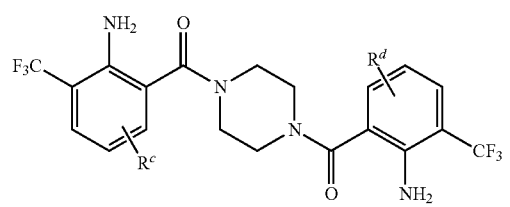
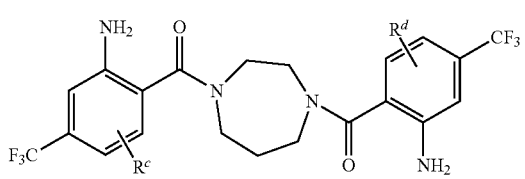
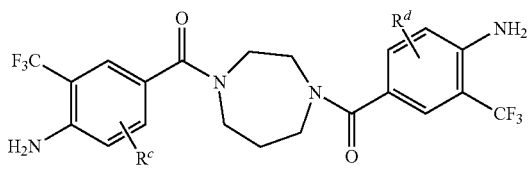
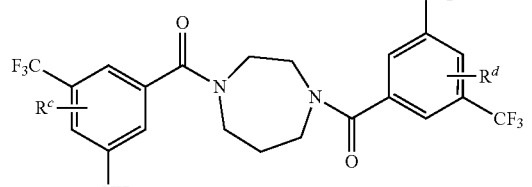
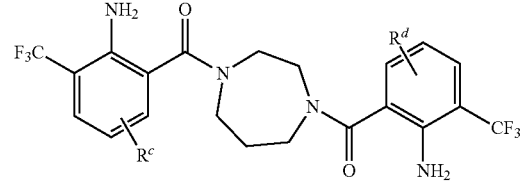
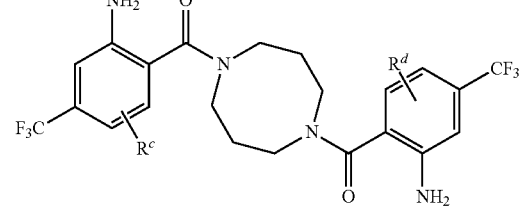
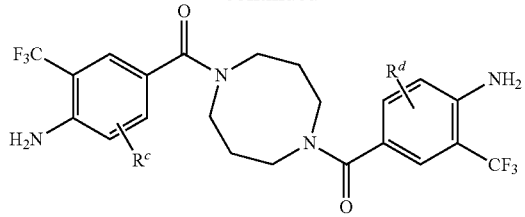
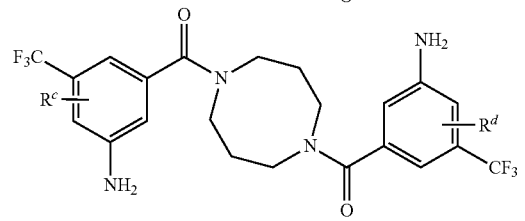
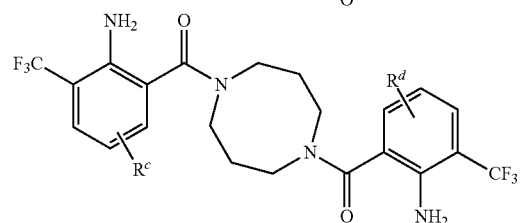
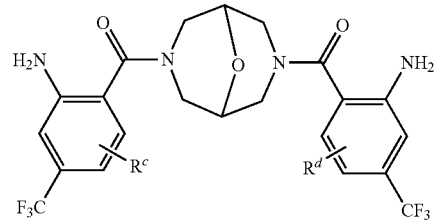
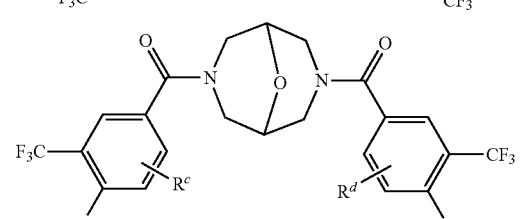
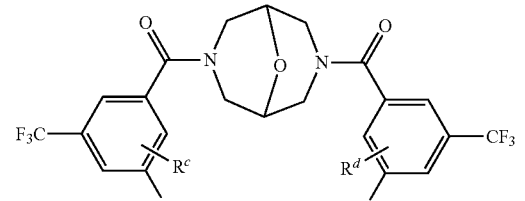
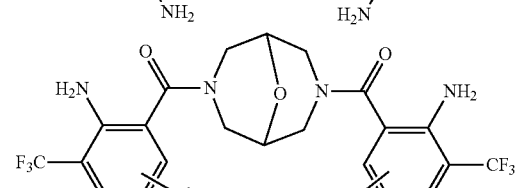
wherein $R^c$ and $R^d$ are independently of each other hydrogen, fluoro, or trifluoromethyl.
The diamine compound according to an exemplary embodiment may be used for polyimide-based polymer synthesis.
In another general aspect, a method of preparing the diamine compound of Chemical Formula 1 is provided.

The method of preparing a diamine compound of the present invention includes: reacting compounds represented by the following Chemical Formulae B-1 and B-2 with a compound of the following Chemical Formula C to prepare a dinitro compound of the following Chemical Formula A; and reducing the dinitro compound of Chemical Formula A to prepare the diamine compound represented by Chemical Formula 1:

[Chemical Formula A]

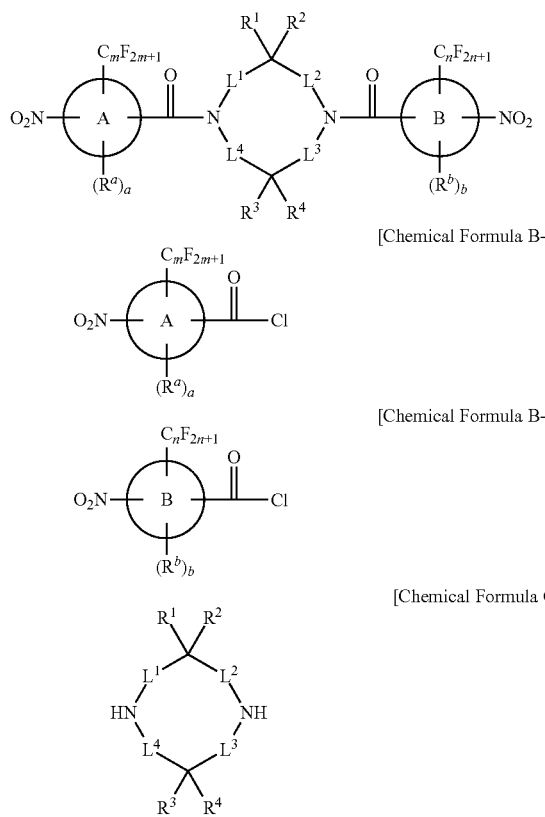

[Chemical Formula B-1]

[Chemical Formula B-2]

[Chemical Formula C]

wherein $L^1$ to $L^4$, $R^1$ to $R^4$, ring A, ring B, $R^a$, $R^b$, a, b, m, and n are as defined in Chemical Formula 1 above.

According to an exemplary embodiment, the reduction of the dinitro compound of Chemical Formula A may be performed in the presence of hydrogen and one or two or more selected from Pd/C, raney-nickel, Rh/C, Pt/C, and Ru/C, or in the presence of iron and acid.

In another general aspect, a polyimide-based polymer composition includes the diamine compound of Chemical Formula 1.

According to an exemplary embodiment, the polyimide-based polymer may be a polyimide, a polyimide precursor, or a mixture thereof.

In another general aspect, a polyimide precursor for manufacturing a polyimide film having improved physical properties is provided, and the polyimide precursor of the present invention includes a structural unit derived from the diamine compound represented by Chemical Formula 1 and a structural unit derived from an acid dianhydride compound.

According to an exemplary embodiment, the acid dianhydride compound may be represented by the following Chemical Formula D:

[Chemical Formula D]

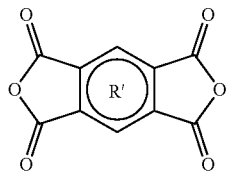

wherein

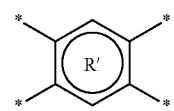

is at least one tetravalent group selected from

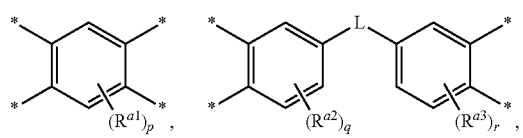

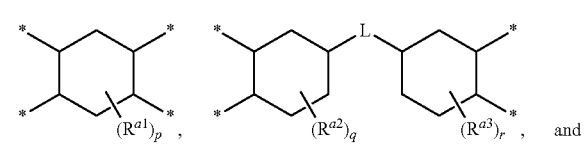

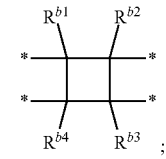

$R^{a1}$, $R^{a2}$, and $R^{a3}$ are independently of one another C1-C10 alkyl or haloC1-C10 alkyl;

L is a single bond, C1-C10 alkylene, —O—, —S—, —CO—, —SO$_2$—, —SiR'R"—, —CO—Ar—CO—, or —O—Ar$^1$—(X—Ar$^2$)$_s$—O—, and the alkylene may be further substituted with one or more selected from C1-C10 alkyl and haloC1-C10 alkyl;

R' and R" are independently of each other C1-C10 alkyl;

Ar, Ar$^1$, and Ar$^2$ are independently of one another C6-C20 arylene, and the arylene may be further substituted with one or more selected from C1-C10 alkyl and haloC1-C10 alkyl;

X is O or S;

$R^{b1}$ to $R^{b4}$ are independently of one another hydrogen, C1-C10 alkyl, or C6-C20 aryl;

p, q, and r are independently of one another an integer of 0 to 2; and s is an integer of 0 or 1.

According to an exemplary embodiment, the polyimide precursor may further include a structural unit derived from a diamine compound represented by the following Chemical Formula E:

[Chemical Formula E]

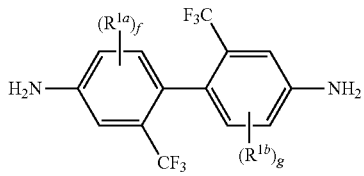

wherein $R^{1a}$ and $R^{1b}$ are independently of each other halogen, C1-C10 alkyl, haloC1-C10 alkyl, C1-C10 alkoxy, or C6-C12 aryl; and f and g are independently of each other an integer of 0 to 3.

According to an exemplary embodiment, the polyimide precursor may include a repeating unit represented by the following Chemical Formula 11:

[Chemical Formula 11]

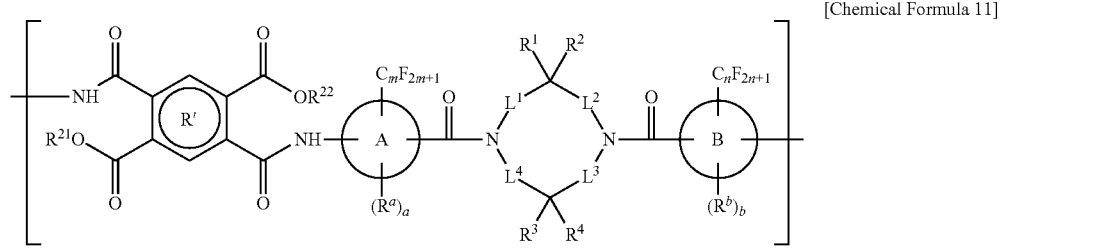

wherein

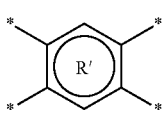

is as defined above for Chemical Formula D;

$R^{21}$ and $R^{22}$ are independently of each other hydrogen or C1-C10 alkyl;

$L^1$ to $L^4$ are independently of one another a single bond or C1-C10 alkylene;

$R^1$ to $R^4$ are independently of one another hydrogen, halogen, C1-C10 alkyl, haloC1-C10 alkyl, C1-C10 alkoxy, C3-C10 cycloalkyl, or C6-C20 aryl, or $R^1$ and $R^3$ may be linked by —NR'—, —O—, or —S—;

R' is hydrogen, C1-C10 alkyl, C3-C10 cycloalkyl, or C6-C20 aryl;

ring A and ring B are independently of each other a C6-C20 aromatic ring;

$R^a$ and $R^b$ are independently of each other halogen, C1-C10 alkyl, haloC1-C10 alkyl, C1-C10 alkoxy, C3-C10 cycloalkyl, or C6-C20 aryl;

a and b are independently of each other an integer of 0 to 3; and m and n are independently of each other an integer of 1 to 10.

In another general aspect, a polyimide film manufactured by using the polyimide precursor is provided.

According to an exemplary embodiment, the polyimide film may include a repeating unit represented by the following Chemical Formula 14:

[Chemical Formula 14]

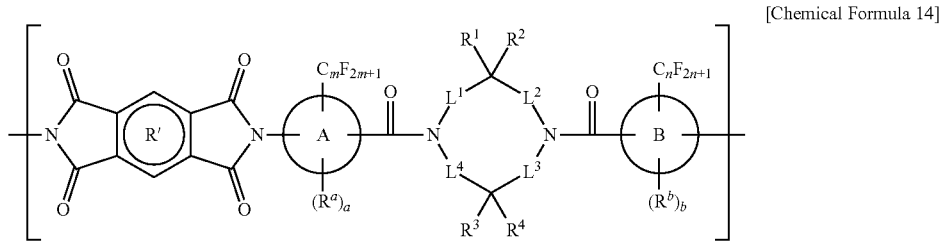

wherein

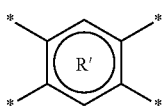

is at least one tetravalent group selected from

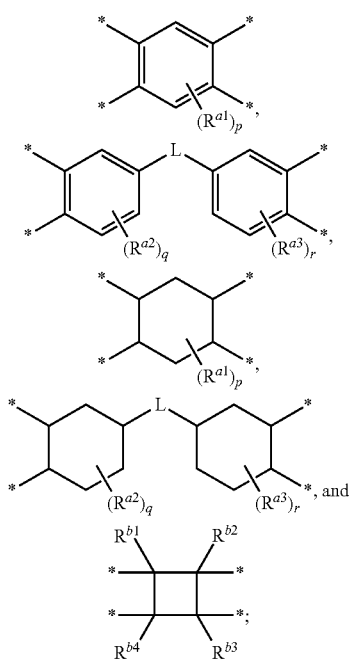

$R^{a1}$, $R^{a2}$, and $R^{a3}$ are independently of one another C1-C10 alkyl or haloC1-C10 alkyl;

L is a single bond, C1-C10 alkylene, —O—, —S—, —CO—, —SO$_2$—, —SiR'R"—, —CO—Ar—CO—, or —O—Ar$^1$—(X—Ar$^2$)$_s$—O—, and the alkylene may be further substituted with one or more selected from C1-C10 alkyl and haloC1-C10 alkyl;

R' and R" are independently of each other C1-C10 alkyl;

Ar, Ar$^1$, and Ar$^2$ are independently of one another C6-C20 arylene, and the arylene may be further substituted with one or more selected from C1-C10 alkyl and haloC1-C10 alkyl;

X is O or S;

$R^{b1}$ to $R^{b4}$ are independently of one another hydrogen, C1-C10 alkyl, or C6-C20 aryl;

$L^1$ to $L^4$ are independently of one another a single bond or C1-C10 alkylene;

$R^1$ to $R^4$ are independently of one another hydrogen, halogen, C1-C10 alkyl, haloC1-C10 alkyl, C1-C10 alkoxy, C3-C10 cycloalkyl, or C6-C20 aryl, or $R^1$ and $R^3$ may be linked to each other by —NR'—, —O—, or —S— to form a ring;

R' is hydrogen, C1-C10 alkyl, C3-C10 cycloalkyl, or C6-C20 aryl;

ring A and ring B are independently of each other a C6-C20 aromatic ring;

$R^a$ and $R^b$ are independently of each other halogen, C1-C10 alkyl, haloC1-C10 alkyl, C1-C10 alkoxy, C3-C10 cycloalkyl, or C6-C20 aryl;

a and b are independently of each other an integer of 0 to 3;

m and n are independently of each other an integer of 1 to 10;

p, q, and r are independently of one another an integer of 0 to 2; and s is an integer of 0 or 1.

According to an exemplary embodiment, the polyimide film may have a retardation value in the thickness direction ($R_{th}$) of 1500 nm or less at a thickness of 50 μm.

According to an exemplary embodiment, the polyimide film may be used in a substrate for a device, a substrate for a display, an optical film, an integrated circuit (IC) package, an electrodeposition film, a multilayer flexible printed circuit (FPC), a tape, a touch panel, or a protective film for an optical disc.

Still another embodiment of the present invention is directed to providing a laminate and a photoelectric device including the polyimide film.

Other features and aspects will be apparent from the following detailed description, the drawings, and the claims.

DESCRIPTION OF THE INVENTION

In the present invention, unless otherwise defined, all technical terms and scientific terms have the same meanings as those commonly understood by a person skilled in the art to which the present invention pertains. The terms used herein are only for effectively describing a certain specific example, and are not intended to limit the present invention.

The singular form used in the present specification may be intended to also include a plural form, unless otherwise indicated in the context.

In addition, units used in the present specification without particular mention are based on weights, and as an example, a unit of % or ratio refers to a wt % or a weight ratio and wt % refers to wt % of any one component in a total composition, unless otherwise defined.

In addition, the numerical range used in the present specification includes all values within the range including the lower limit and the upper limit, increments logically derived in a form and span in a defined range, all double limited values, and all possible combinations of the upper limit and the lower limit in the numerical range defined in different forms. Unless otherwise defined in the specification of the present invention, values which may be outside a numerical range due to experimental error or rounding of a value are also included in the defined numerical range.

The term of the present specification "comprise" is an open-ended description having a meaning equivalent to the term such as "is/are provided", "contain", "have", or "is/are characterized", and does not exclude elements, materials or processes which are not further listed.

The term "polyimide precursor composition", "polyimide precursor solution", "polyimide-based polymer composition", and "polyimide-based polymer solution" in the present specification refer to a composition for preparing a polyimide-based polymer, and specifically, the polyimide precursor may have an equivalent meaning to a polyamic acid or a polyamic acid ester. In addition, the polyimide precursor solution may be used as a composition for preparing polyamideimide.

The term "polyimide film" in the present specification may be a molded body of a polyimide derived from a polyimide precursor composition, a polyimide precursor solution, a polyimide-based polymer composition, or a polyimide-based polymer solution, and may have an equivalent meaning to polyimide.

The term "polyimide-based polymer" in the present specification refers to inclusion of both a polyimide and a polyimide precursor (that is, a polyamic acid or a polyamic acid ester).

The term "$C_A$-$C_B$" in the present specification refers to "having A or more and B or fewer carbon atoms", and the term "A to B" refers to "A or more and B or less"

The term "halogen" in the present specification refers to fluorine (F), chlorine (Cl), bromine (Be), or iodine (I) atom.

The term "alkyl" in the present specification is an organic radical derived from an aliphatic hydrocarbon by removal of one hydrogen, and includes both a straight chain and branched chain forms.

The term "alkoxy" in the present specification is indicated as *—O-alkyl, and the alkyl is as defined above.

The term "haloalkyl" in the present specification refers to alkyl in which at least one hydrogen is replaced with a halogen.

The term "aryl" in the present specification refers to an organic radical derived from an aromatic hydrocarbon by removal of one hydrogen, and includes suitably a monocyclic or fused ring system containing suitably 4 to 7, preferably 5 or 6 ring atoms in each ring, and even a form in which a plurality of aryls are connected by a single bond. As an example, phenyl, naphthyl, biphenyl, fluorenyl, and the like are included, but the present invention is not limited thereto.

The term "aromatic" in the present specification is a characteristic satisfying Huckel's rule, and according to the Huckel's rule, it refers to the case in which i) there are 4n+2 electrons which completely form a conjugation by an empty p-orbital, an unsaturated bond, lone pairs of electrons, and the like, and ii) the 4n+2 electrons form a planar conformation isomer and forms a ring structure; and also iii) all atoms in the ring should participate in conjugation.

The term "arylene" in the present specification is a divalent functional group derived from arene, and the description for aryl may be applied except that it is a divalent functional group. For example, it may be phenylene, biphenylene, terphenylene, naphthalene, fluorenylene, pyrenylene, phenanthrenylene, perylene, anthracenylene, and the like.

The present invention provides a diamine compound having a structure, and the diamine compound having a structure of the present invention is represented by the following Chemical Formula 1:

[Chemical Formula 1]

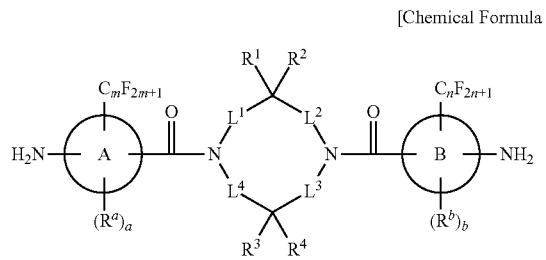

wherein $L^1$ to $L^4$ are independently of one another a single bond or C1-C10 alkylene;

$R^1$ to $R^4$ are independently of one another hydrogen, halogen, C1-C10 alkyl, haloC1-C10 alkyl, C1-C10 alkoxy, C3-C10 cycloalkyl, or C6-C20 aryl, or $R^4$ and $R^3$ may be linked to each other by —NR'—, —O—, or —S— to form a ring;

R' is hydrogen, C1-C10 alkyl, C3-C10 cycloalkyl, or C6-C20 aryl;

ring A and ring B are independently of each other a C6-C20 aromatic ring;

$R^a$ and $R^b$ are independently of each other halogen, C1-C10 alkyl, haloC1-C10 alkyl, C1-C10 alkoxy, C3-C10 cycloalkyl, or C6-C20 aryl;

a and b are independently of each other an integer of 0 to 3; and m and n are independently of each other an integer of 1 to 10.

The diamine compound having a structure according to the present invention has a structure in which an aromatic ring to which a fluoro-substituted alkyl group and an amino group are introduced is connected to a nitrogen atom-containing ring having a specific structure by an amide bond, and may be used as a diamine monomer to manufacture a highly transparent polyimide film having improved physical properties, in particular, retardation improvement properties, through polymerization with an acid dianhydride.

Preferably, in Chemical Formula 1 according to an exemplary embodiment of the present invention, $L^1$ and $L^3$ may be independently of each other a single bond or C1-C5 alkylene; $L^2$ and $L^4$ may be independently of each other C1-C5 alkylene; and ring A and ring B may be independently of each other benzene or naphthalene.

In terms of preparing a polyimide having more improved physical properties, Chemical Formula 1 according to an exemplary embodiment of the present invention may be represented by the following Chemical Formula 2 or Chemical Formula 3:

[Chemical Formula 2]

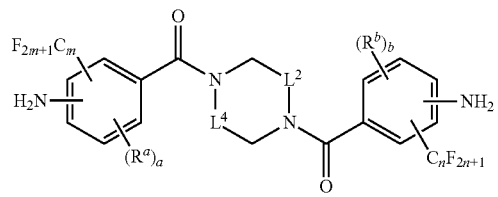

[Chemical Formula 3]

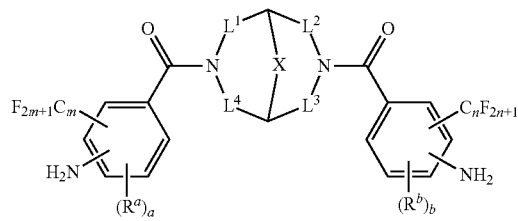

wherein $L^1$ to $L^4$ are independently of one another C1-C5 alkylene;

X is —NR'—, —O—, or —S—;

R' is hydrogen or C1-C5 alkyl;

$R^a$ and $R^b$ are independently of each other halogen, C1-C5 alkyl, haloC1-C5 alkyl, C1-C5 alkoxy, C3-C7 cycloalkyl, or C6-C12 aryl;

a and b are independently of each other an integer of 0 or 1; and m and n are independently of each other an integer of 1 to 5.

Chemical Formula 2 according to an exemplary embodiment of the present invention may be represented by the following Chemical Formula 4:

[Chemical Formula 4]

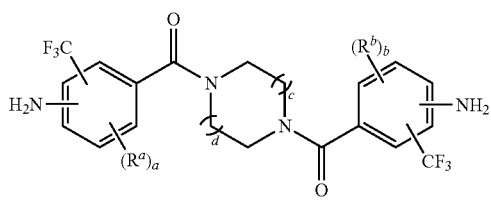

wherein $R^a$ and $R^b$ are independently of each other halogen, C1-C5 alkyl, or haloC1-C5 alkyl;

a and b are independently of each other an integer of 0 or 1; and c and d are independently of each other an integer of 1 or 2.

Chemical Formula 3 according to an exemplary embodiment of the present invention may be represented by the following Chemical Formula 5:

[Chemical Formula 5]

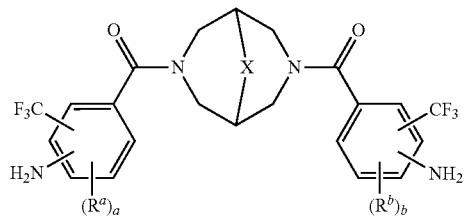

wherein

X is —O— or —S—;

$R^a$ and $R^b$ are independently of each other halogen, C1-C5 alkyl, or haloC1-C5 alkyl; and a and b are independently of each other an integer of 0 or 1.

The diamine compound according to an exemplary embodiment of the present invention is useful as a diamine monomer for synthesizing a polyimide which may implement excellent transparency, high heat resistance, and a low retardation.

In particular, the diamine compound of Chemical Formulae 4 and 5 may produce a highly transparent polyimide having a low retardation due to a structure in which a benzene ring to which a trifluoromethyl group and an amino group are introduced is connected to a nitrogen atom-containing ring having a specific structure by an amide bond. In addition, a polyimide which has no problems of bending, peeling off, and breakage even with a heat treatment performed in the preparation of polyimide and has uniform transmittance and transparency may be prepared. That is, the diamine compound of Chemical Formulae 4 and 5 is very appropriate as a diamine compound for synthesizing a polyimide-based polymer having excellent transparency, high heat resistance, and a low retardation.

The diamine compound according to an exemplary embodiment of the present invention may be specifically selected from the following compounds, but is not limited thereto:

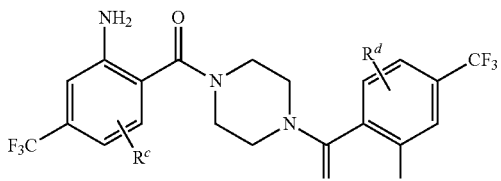

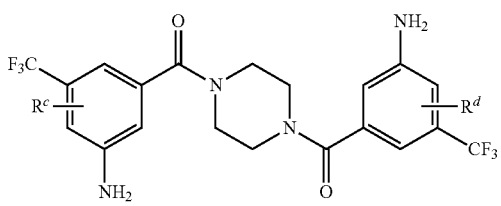

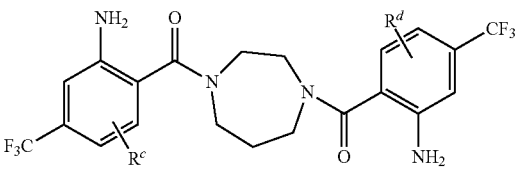

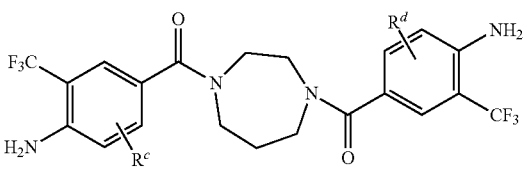

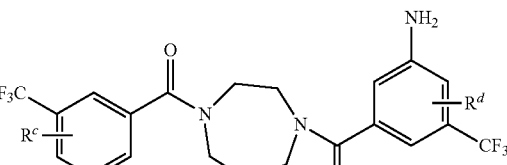

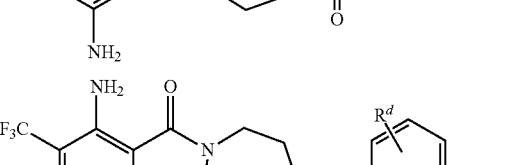

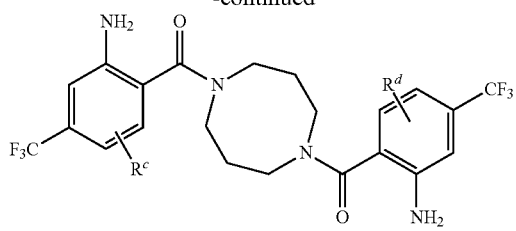
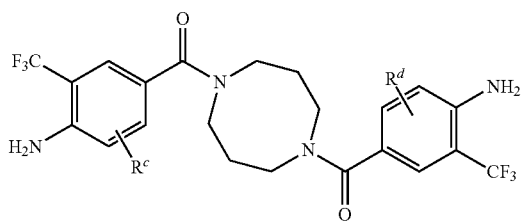
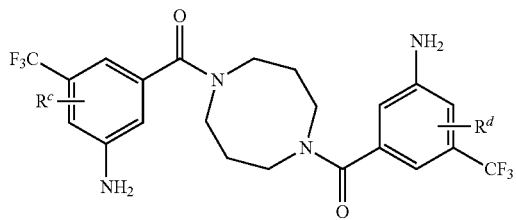
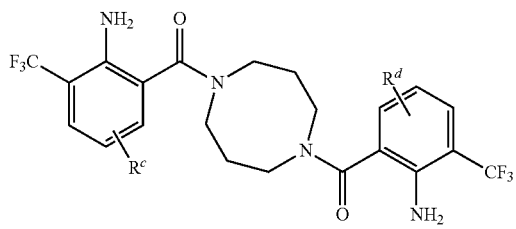
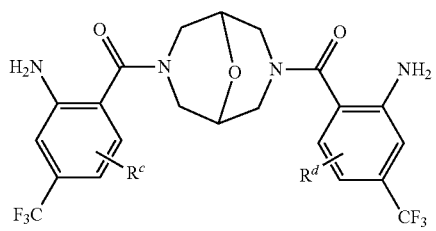
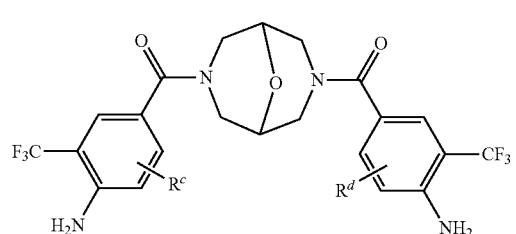
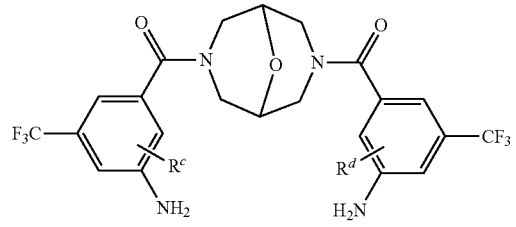

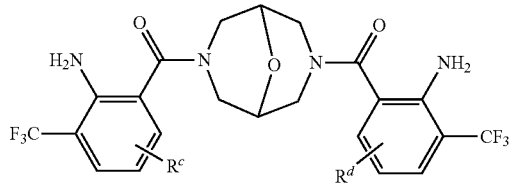

wherein $R^c$ and $R^d$ are independently of each other hydrogen, fluoro, or trifluoromethyl.

Chemical Formula 4 according to an exemplary embodiment of the present invention may be represented by the following Chemical Formula 4-1:

[Chemical Formula 4-1]

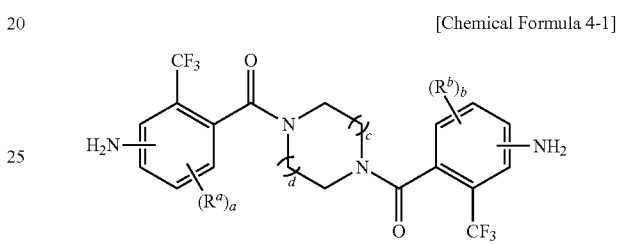

wherein $R^a$ and $R^b$ are independently of each other halogen, C1-C5 alkyl, or haloC1-C5 alkyl;

a and b are independently of each other an integer of 0 or 1; and c and d are independently of each other an integer of 1 or 2.

Preferably, Chemical Formula 4 according to an exemplary embodiment of the present invention may be represented by the following Chemical Formula 4-2:

[Chemical Formula 4-2]

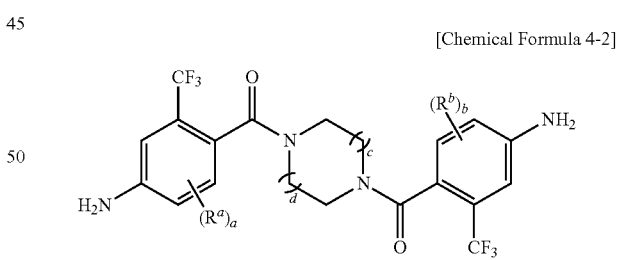

wherein $R^a$ and $R^b$ are independently of each other halogen or haloC1-C5 alkyl.

a and b are independently of each other an integer of 0 or 1; and c and d are independently of each other an integer of 1 or 2.

Chemical Formula 5 according to an exemplary embodiment of the present invention may be represented by the following Chemical Formula 5-1:

[Chemical Formula 5-1]

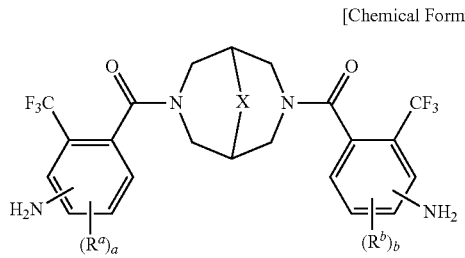

wherein x is —O— or —S—;

$R^a$ and $R^b$ are independently of each other halogen, C1-C5 alkyl, or haloC1-C5 alkyl; and a and b are independently of each other an integer of 0 or 1.

Preferably, Chemical Formula 5 according to an exemplary embodiment of the present invention may be represented by the following Chemical Formula 5-2:

[Chemical Formula 5-2]

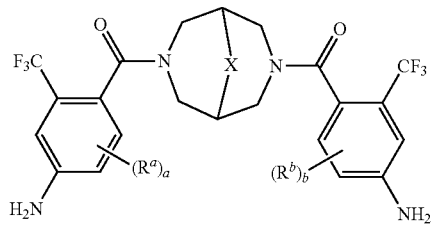

wherein

X is —O— or —S—;

$R^a$ and $R^b$ are independently of each other halogen or haloC1-C5 alkyl; and a and b are independently of each other an integer of 0 or 1.

The diamine compound according to an exemplary embodiment of the present invention may be specifically selected from the following compounds, but is not limited thereto:

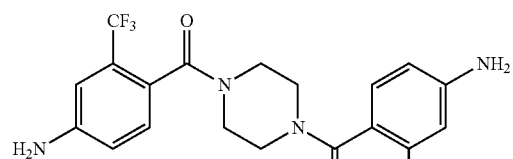

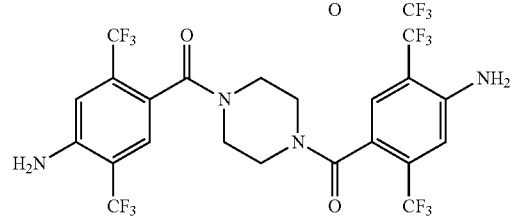

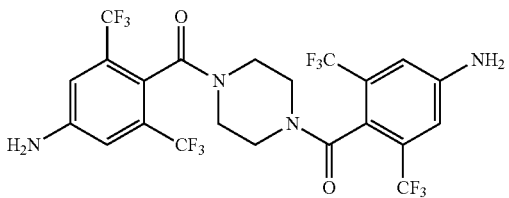

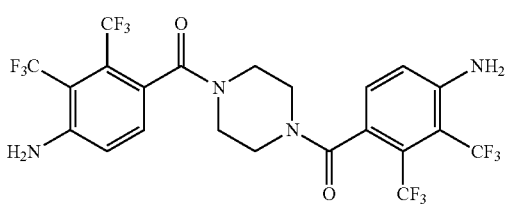

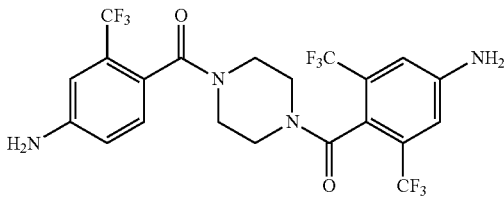

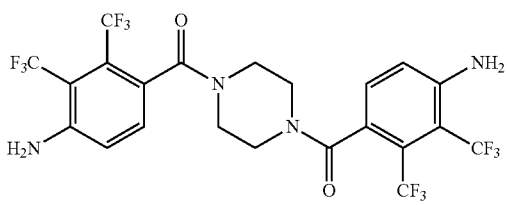

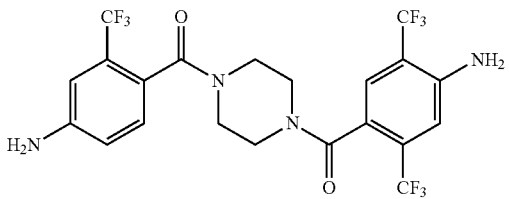

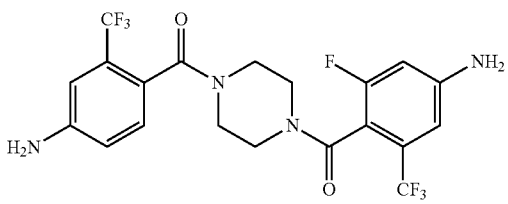

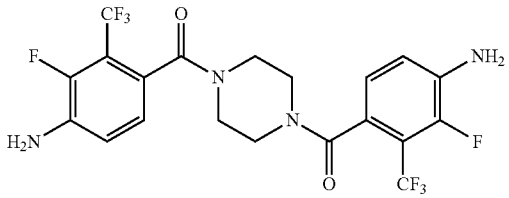

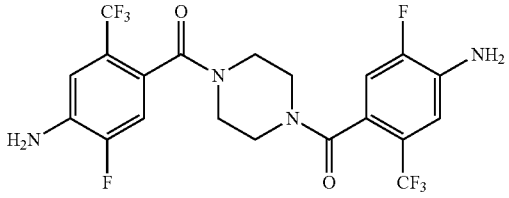

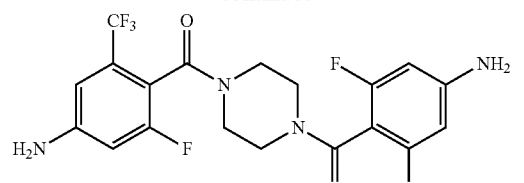
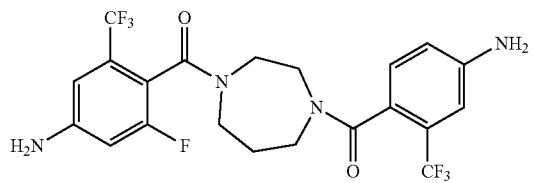
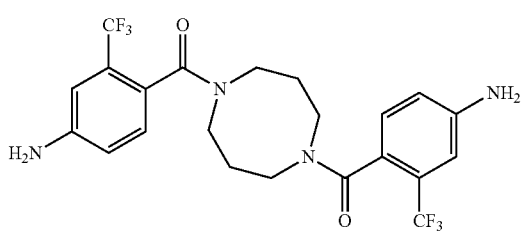
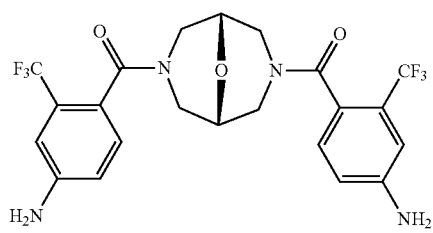
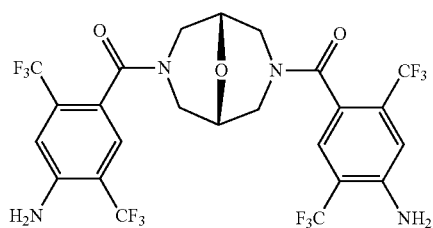
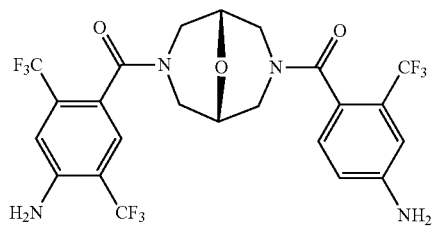
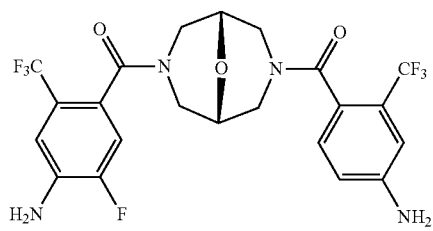

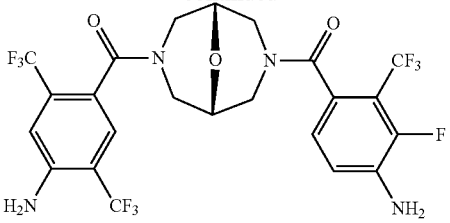

The diamine compound according to an exemplary embodiment of the present invention may be reacted with an acid dianhydride compound to synthesize a polyimide precursor (that is, a polyamic acid or polyamic acid ester), as described later, and a polyimide may be synthesized by imidizing the polyimide precursor. That is, the diamine compound according to an exemplary embodiment may be applied as a monomer for synthesizing a polyimide-based polymer. Herein, the polyimide-based polymer refers to inclusion of both a polyimide and a polyimide precursor (that is, a polyamic acid or a polyamic acid ester).

In addition, the present invention provides a method of preparing the diamine compound having a structure, and the method of preparing a diamine compound having a structure includes: reacting compounds represented by the following Chemical Formulae B-1 and B-2 with a compound of the following Chemical Formula C to prepare a dinitro compound of the following Chemical Formula A; and reducing the dinitro compound of Chemical Formula A to prepare the diamine compound represented by Chemical Formula 1:

[Chemical Formula A]

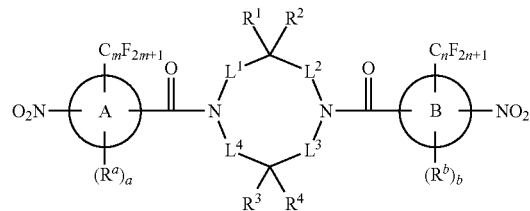

[Chemical Formula B-1]

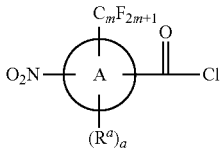

[Chemical Formula B-2]

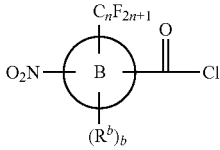

[Chemical Formula C]

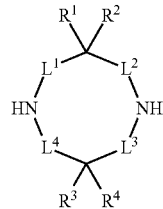

wherein $L^1$ to $L^4$, $R^1$ to $R^4$, ring A, ring B, $R^a$, $R^b$, a, b, m, and n are as defined in Chemical Formula 1 above.

According to an exemplary embodiment, the reduction of the dinitro compound of Chemical Formula A may be performed by introducing hydrogen in the presence of a transition metal catalyst, and specifically, may be performed in the presence of hydrogen and one or two or more selected from Pd/C, raney-nickel, Rh/C, Pt/C, and Ru/C, or in the presence of iron and acid.

In an exemplary embodiment, the reduction reaction may be performed at 5 to 60° C. for 1 to 24 hours, specifically 20 to 50° C. for 1 to 10 hours, and more specifically 20 to 35° C. for 2 to 8 hours.

In addition, the present invention provides a polyimide precursor prepared using the diamine compound having a structure as a monomer, and the polyimide precursor according to an exemplary embodiment includes a structural unit derived from the diamine compound of Chemical Formula 1 and a structural unit derived from an acid dianhydride compound.

That is, the polyimide precursor according to an exemplary embodiment may include a repeating unit in which a bond between a nitrogen atom of an amino group and a carbon atom of an anhydride group is formed by a reaction of a terminal amino group (—NH$_2$) of the diamine compound and a terminal anhydride group (—OC—O—CO—) of the acid dianhydride compound.

The polyimide precursor according to the present invention includes a structural unit derived from a diamine compound having a structure in which an aromatic ring to which a fluoro-substituted alkyl group and an amino group are introduced is connected to a nitrogen-containing ring having a specific structure by an amide bond, and thus, a polyimide prepared by cyclizing the structural unit may have extremely improved low retardation properties, in addition to excellent heat resistance and transparency.

The polyimide precursor according to an exemplary embodiment of the present invention may further include a structural unit derived from a known diamine compound, in addition to the structural unit derived from the diamine compound represented by Chemical Formula 1. An example of the known diamine compound which is further included may include 4,4'-diaminodiphenylpropane, 4,4'-diaminodiphenylmethane, 4,4'-diaminodiphenylsulfide, 3,3'-diaminodiphenylsulfone, 4,4'-diaminodiphenylsulfone, 4,4'-oxydianiline, 3,3'-oxydianiline, 3,4'-oxydianiline, 4,4'-diaminodiphenyl diethylsilane, 4,4'-diaminodiphenylsilane, 4,4'-diaminodiphenylethylphosphineoxide, 4,4'-diaminodiphenyl N-methylamine, 4,4'-diaminodiphenyl N-phenylamine, 1,4-diaminobenzene(p-phenylenediamine), bis{4-(4-aminophenoxy)phenyl}sulfone, bis{4-(3-aminophenoxy)phenyl}sulfone, 4,4'-bis(4-aminophenoxy)biphenyl, 4,4'-bis(3-aminophenoxy)biphenyl, 1,3-bis(3-aminophenoxy)benzene, 1,3-bis(4-aminophenoxy)benzene, 3,3'-diaminobenzophenone, 4,4'-diaminobenzophenone, 2,2-bis(4-aminophenoxyphenyl)propane, and the like, and these may be used alone or in combination, but the present invention is not limited thereto.

The polyimide precursor according to an exemplary embodiment may further include a structural unit derived from a diamine compound represented by the following Chemical Formula E:

[Chemical Formula E]

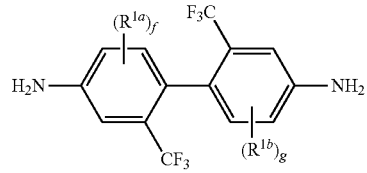

wherein $R^{1a}$ and $R^{1b}$ are independently of each other halogen, C1-C10 alkyl, haloC1-C10 alkyl, C1-C10 alkoxy, or C6-C12 aryl; and f and g are independently of each other an integer of 0 to 3.

Preferably, in Chemical Formula E, $R^{1a}$ and $R^{1b}$ may be independently of each other halogen, C1-C5 alkyl, or haloC1-C5 alkyl; and f and g may be independently of each other an integer of 0 or 1, more preferably, f and g may be 0.

In an exemplary embodiment, when the polyimide precursor is prepared by including the known diamine compound which is further included as a monomer, a ratio of the diamine compound represented by Chemical Formula 1 as a monomer may be 0.1 to 99 mol %, preferably 10 to 90 mol %, and more preferably 10 to 80 mol % with respect to a total content of the diamine compound represented by Chemical Formula 1 and the known diamine compound, specifically the diamine compound of Chemical Formula E. When the diamine compound of Chemical Formula 1 is used in the above range, the effect of improving a retardation may be maximized.

In an exemplary embodiment of the present invention, any acid dianhydride compound may be used as long as it has an acid dianhydride functional group, but specifically, may be a tetracarboxylic acid dianhydride, and the tetracarboxylic acid dianhydride may be at least one selected from C8-C36 aromatic tetracarboxylic acid dianhydride, C6-C50 aliphatic tetracarboxylic acid dianhydride, and C6-C36 alicyclic tetracarboxylic acid dianhydride. That is, the tetracarboxylic acid compound may be used alone or in combination of two or more. In terms of having an excellent yellow index even in a high temperature range, the acid dianhydride compound may be preferably a C8-C36 aromatic tetracarboxylic acid dianhydride. The number of carbons in the tetracarboxylic acid dianhydride according to an exemplary embodiment includes the number of carbons included in a carboxyl group.

In a specific example, the C8-C36 aromatic tetracarboxylic acid dianhydride may include 4,4'-(hexafluoroisopropylidene)diphthalic acid anhydride (6FDA), 5-(2,5-dioxotetrahydro-3-furanyl)-3-methyl-cyclohexene-1,2-dicarboxylic acid anhydride, pyromellitic dianhydride, 1,2,3,4-benzenetetracarboxylic acid dianhydride, 3,3',4,4'-benzophenonetetracarboxylic acid dianhydride, 2,2',3,3'-benzophenonetetracarboxylic acid dianhydride, 3,3',4,4'-biphenyltetracarboxylic acid dianhydride, 3,3',4,4'-diphenylsulfonetetracarboxylic acid dianhydride, 2,2',3,3'-biphenyltetracarboxylic acid dianhydride, methylene-4,4'-diphthalic acid dianhydride, 1,1-ethylidene-4,4'-diphthalic acid dianhydride, 2,2-propylidene-4,4'-diphthalic acid dianhydride, 1,2-ethylene-4,4'-diphthalic acid dianhydride, 1,3-trimethylene-4,4'-diphthalic acid dianhydride, 1,4-tetramethylene-4,4'-diphthalic acid dianhydride, 1,5-pentamethylene-4,4'-diphthalic acid dianhydride, 4,4'- oxydiphthalic acid dianhydride, p-phenylenebis(trimellitate acid anhydride), thio-4,4'-diphthalic dianhydride, sulfonyl-4,4'-diphthalic acid dianhydride, 1,3-bis(3,4-dicarboxyphenyl)benzene dianhydride, 1,3-bis(3,4-dicarboxyphenoxy)benzene dianhydride, 1,4-bis(3,4-dicarboxyphenoxy)benzene dianhydride, 1,3-bis[2-(3,4-dicarboxyphenyl)-2-propyl]benzene dianhydride, 1,4-bis[2-(3,4-dicarboxyphenyl)-2-propyl]benzene dianhydride, bis[3-(3,4-dicarboxyphenoxy)phenyl]methane dianhydride, bis[4-(3,4-dicarboxyphenoxy)phenyl]methane dianhydride, 2,2-bis[3-(3,4-dicarboxyphenoxy)phenyl]propane dianhydride, 2,2-bis[4-(3,4-dicarboxyphenoxy)phenyl]propane dianhydride, bis(3,4-dicarboxyphenoxy)dimethylsilane dianhydride, 1,3-bis(3,4-dicarboxyphenyl)-1,1,3,3-tetramethyldisiloxane dianhydride, 2,3,6,7-naphthalenetetracarboxylic acid dianhydride, 1,4,5,8-naphthalenetetracarboxylic acid dianhydride, 1,2,5,6-naphthalenetetracarboxylic acid dianhydride, 3,4,9,10-pyrylenetetracarboxylic acid dianhydride, 2,3,6,7-anthracenetetracarboxylic acid dianhydride, 1,2,7,8-phenanthrenetetracarboxylic acid dianhydride, and the like, the C6-C50 aliphatic tetracarboxylic acid dianhydride may include, specifically, ethylenetetracarboxylic acid dianhydride, 1,2,3,4-butanetetracarboxylic acid dianhydride, 1,2,3,4-pentanetetracarboxylic acid dianhydride, and the like, and the C6-C36 alicyclic tetracarboxylic acid dianhydride may include, specifically, 1,2,3,4-cyclobutanetetracarboxylic acid dianhydride, cyclopentanetetracarboxylic acid dianhydride, cyclohexane-1,2,3,4-tetracarboxylic acid dianhydride, cyclohexane-1,2,4,5-tetracarboxylic acid dianhydride, 3,3',4,4'-bicyclohexyltetracarboxylic acid dianhydride, carbonyl-4,4'-bis(cyclohexane-1,2-dicarboxylic acid) dianhydride, methylene-4,4'-bis(cyclohexane-1,2-dicarboxylic acid) dianhydride, 1,2-ethylene-4,4'-bis(cyclohexane-1,2-dicarboxylic acid) dianhydride, 1,1-ethylidene-4,4'-bis(cyclohexane-1,2-dicarboxylic acid) dianhydride, 2,2-propylidene-4,4'-bis(cyclohexane-1,2-dicarboxylic acid) dianhydride, oxy4,4'-bis(cyclohexane-1,2-dicarboxylic acid) dianhydride, thio-4,4'-bis(cyclohexane-1,2-dicarboxylic acid) dianhydride, sulfonyl-4,4'-bis(cyclohexane-1,2-dicarboxylic acid) dianhydride, bicyclo[2,2,2]oct-7-ene-2,3,5,6-tetracarboxylic acid dianhydride, 4-(2,5-dioxotetrahydrofuran-3-yl)-1,2,3,4-tetrahydronaphthalene-1,2-dicarboxylic acid anhydride, ethyleneglycol-bis-(3,4-dicarboxylic acid anhydride phenyl)ether, and the like. These may be used alone or in combination of two or more.

In terms of implementing excellent chemical resistance, yellow index, and the like, more preferably, the acid dianhydride compound according to an exemplary embodiment may be an acid dianhydride compound represented by the following Chemical Formula D:

[Chemical Formula D]

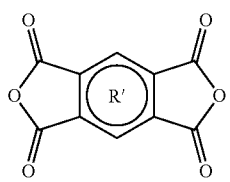

wherein

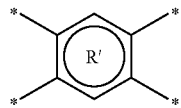

is at least one tetravalent group selected from

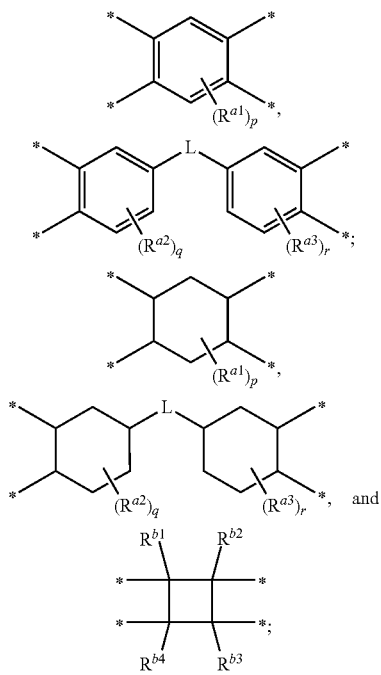

$R^{a1}$, $R^{a2}$, and $R^{a3}$ are independently of one another C1-C10 alkyl or haloC1-C10 alkyl;

L is a single bond, C1-C10 alkylene, —O—, —S—, —CO—, —SO$_2$—, —SiR'R"—, —CO—Ar—CO—, or —O—Ar$^1$—(X—Ar$^2$)$_s$—O—, and the alkylene may be further substituted with one or more selected from C1-C10 alkyl and haloC1-C10 alkyl;

R' and R" are independently of each other C1-C10 alkyl;

Ar, Ar$^1$, and Ar$^2$ are independently of one another C6-C20 arylene, and the arylene may be further substituted with one or more selected from C1-C10 alkyl and haloC1-C10 alkyl;

x is O or S;

$R^{b1}$ to $R^{b4}$ are independently of one another hydrogen, C1-C10 alkyl, or C6-C20 aryl;

p, q, and r are independently of one another an integer of 0 to 2; and s is an integer of 0 or 1.

In Chemical Formula D according to an exemplary embodiment,

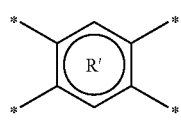

may be

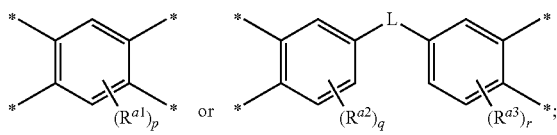

$R^{a1}$, $R^{a2}$, and $R^{a3}$ may be independently of one another C1-C5 alkyl or haloC1-C5 alkyl; L may be C1-C5 alkylene, —O—, —S—, —CO—, or —SO$_2$—, and the alkylene may be further substituted with one or more selected from C1-C5 alkyl and haloC1-C5 alkyl; and p, q, and r may be independently of one another an integer of 0 or 1.

Preferably, in Chemical Formula D according to an exemplary embodiment,

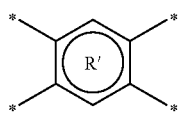

may be

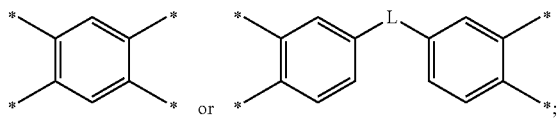

L may be —$CR^{c1}R^{c2}$—; $R^{c1}$ and $R^{c2}$ may be independently of each other C1-C3 alkyl or haloC1-C3 alkyl, and more preferably, $R^{c1}$ and $R^{c2}$ may be independently of each other $CH_3$ or $CF_3$.

The polyimide precursor according to an exemplary embodiment may include a repeating unit represented by the following Chemical Formula 11:

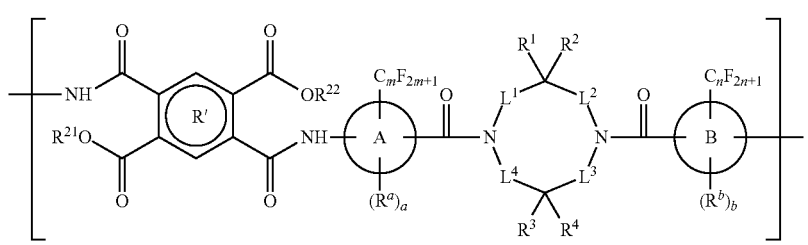

wherein

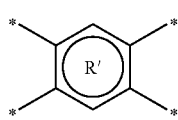

is as defined above for Chemical Formula D;

$R^{21}$ and $R^{22}$ are independently of each other hydrogen or C1-C10 alkyl;

$L^1$ to $L^4$ are independently of one another a single bond or C1-C10 alkylene;

$R^1$ to $R^4$ are independently of one another hydrogen, halogen, C1-C10 alkyl, haloC1-C10 alkyl, C1-C10 alkoxy, C3-C10 cycloalkyl, or C6-C20 aryl, or $R^1$ and $R^3$ may be linked to each other by —NR'—, —O—, or —S— to form a ring;

R' is hydrogen, C1-C10 alkyl, C3-C10 cycloalkyl, or C6-C20 aryl;

ring A and ring B are independently of each other a C6-C20 aromatic ring;

$R^a$ and $R^b$ are independently of each other halogen, C1-C10 alkyl, haloC1-C10 alkyl, C1-C10 alkoxy, C3-C10 cycloalkyl, or C6-C20 aryl;

a and b are independently of each other an integer of 0 to 3; and m and n are independently of each other an integer of 1 to 10.

In Chemical Formula 11 according to an exemplary embodiment, ring A and ring B may be independently of each other benzene or naphthalene;

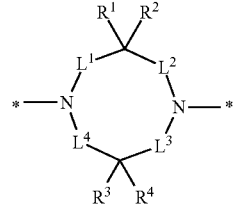

[Chemical Formula 11]

may be

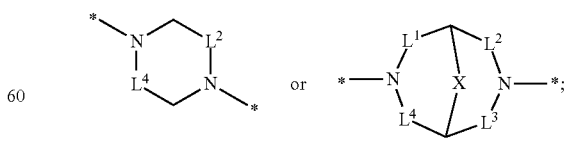

$L^1$ to $L^4$ may be independently of one another C1-C5 alkylene; X may be —NR'—, —O—, or —S-|⊼; R' may be hydrogen or C1-C5 alkyl; $R^a$ and $R^b$ may be independently of each other halogen, C1-C5 alkyl, haloC1-C5 alkyl, C1-C5 alkoxy, C3-C7 cycloalkyl, or C6-C12 aryl;

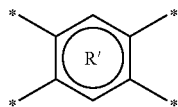

may be

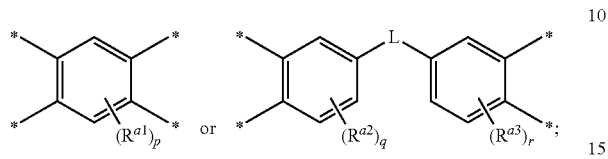

$R^{a1}$, $R^{a2}$, and $R^{a3}$ may be independently of one another C1-C5 alkyl or haloC1-C5 alkyl; $R^{21}$ and $R^{22}$ may be independently of each other hydrogen or C1-C5 alkyl; L may be a single bond, C1-C5 alkylene, —O—, —S—, —CO—, or —SO$_2$—, and the alkylene may be further substituted with one or more selected from C1-C5 alkyl and haloC1-C5 alkyl; a and b may be independently of each other an integer of 0 or 1; m and n may be independently of each other an integer of 1 to 5; and p, q, and r may be independently of one another an integer of 0 or 1.

The polyimide precursor according to an exemplary embodiment may include a repeating unit represented by the following Chemical Formula 12 or 13:

[Chemical Formula 12]

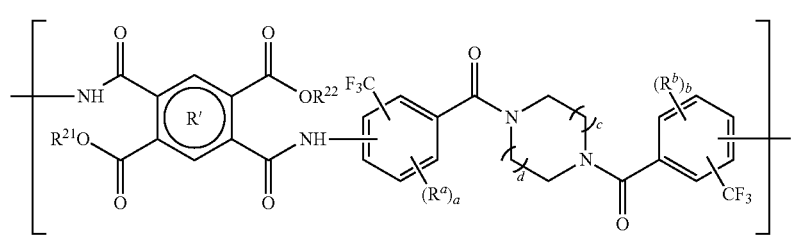

[Chemical Formula 13]

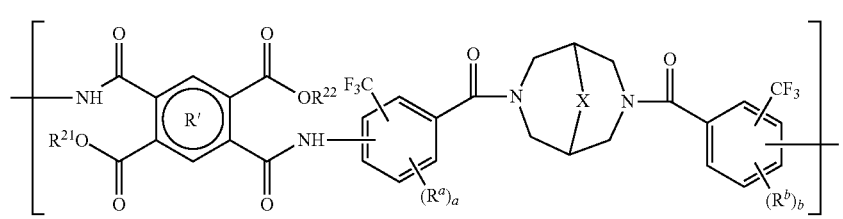

wherein

X is —O— or —S—;

$R^a$ and $R^b$ are independently of each other halogen, C1-C5 alkyl, or haloC1-C5 alkyl;

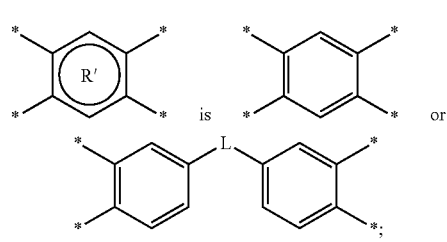

$R^{21}$ and $R^{22}$ are independently of each other hydrogen or C1-C5 alkyl;

L is a single bond or —$CR^{c1}R^{c2}$—;

$R^{c1}$ and $R^{c2}$ are independently of each other C1-C3 alkyl or haloC1-C3 alkyl;

a and b are independently of each other an integer of 0 or 1; and c and d are independently of each other an integer of 1 or 2.

The polyimide precursor according to an exemplary embodiment may include a repeating unit represented by the following Chemical Formula 12-1 or 13-1:

[Chemical Formula 12-1]

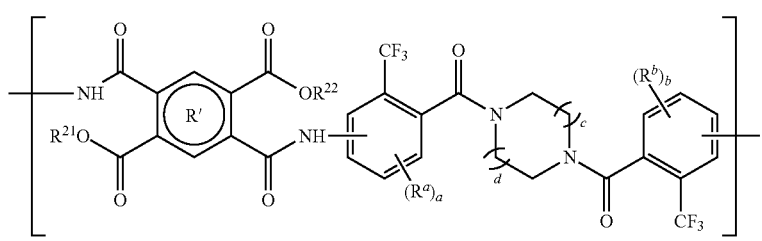

[Chemical Formula 13-1]

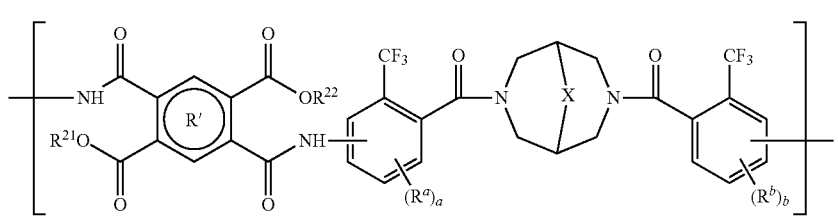

wherein
X is —O— or —S—;
$R^a$ and $R^b$ are independently of each other halogen, C1-C5 alkyl, or haloC1-C5 alkyl;

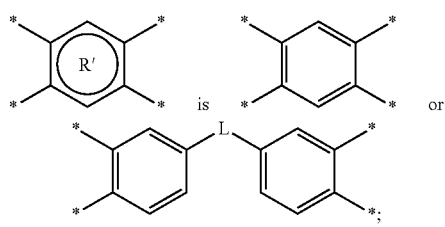

is $R^{21}$ and $R^{22}$ are independently of each other hydrogen or C1-C5 alkyl;

L is a single bond or —$CR^{c1}$—$R^{c2}$—;

$R^{c1}$ and $R^{c2}$ are independently of each other C1-C3 alkyl or haloC1-C3 alkyl;

a and b are independently of each other an integer of 0 or 1; and c and d are independently of each other an integer of 1 or 2.

Preferably, the polyimide precursor according to an exemplary embodiment may include a repeating unit represented by the following Chemical Formula 12-2 or 13-2:

[Chemical Formula 12-2]

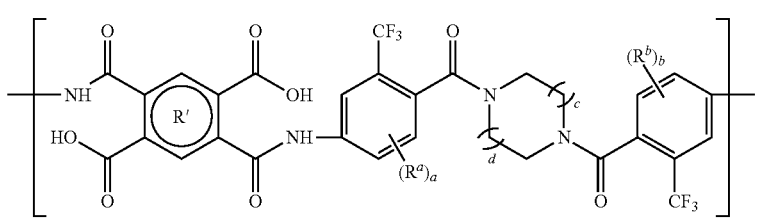

[Chemical Formula 13-2]

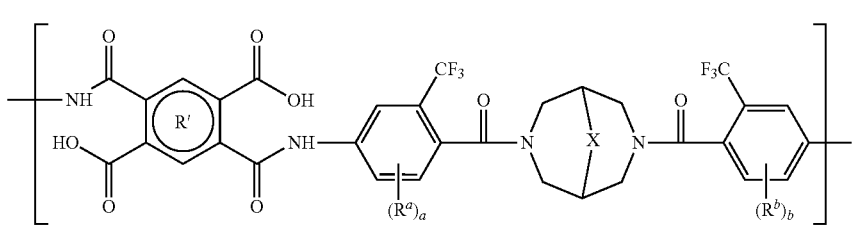

wherein

X is —O— or —S—;

$R^a$ and $R^b$ are independently of each other halogen or haloC1-C5 alkyl.

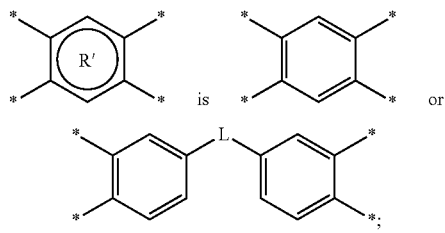 is

L is a single bond or —$CR^{c1}R^{c2}$—;

$R^{c1}$ and $R^{c2}$ are independently of each other C1-C3 alkyl or haloC1-C3 alkyl;

a and b are independently of each other an integer of 0 or 1; and c and d are independently of each other an integer of 1 or 2.

Specifically, in Chemical Formulae 12 and 13 according to an exemplary embodiment, X may be —O—.

Specifically, in Chemical Formulae 12 and 13 according to an exemplary embodiment, c and d may be independently of each other an integer of 1.

Specifically, in Chemical Formulae 12 and 13 according to an exemplary embodiment, a and b may be independently of each other 0.

Specifically, in Chemical Formulae 12 and 13 according to an exemplary embodiment,

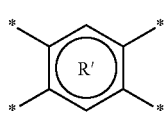

may be

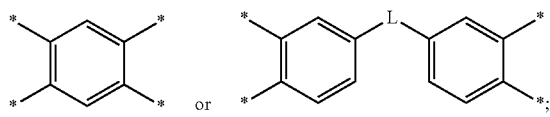

L may be —$CR^{c1}R^{c2}$—; and $R^{c1}$ and $R^{c2}$ may be independently of each other $CH_3$ or $CF_3$.

More specifically, in Chemical Formulae 12 and 13 according to an exemplary embodiment, X may be —O—;

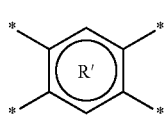

may be

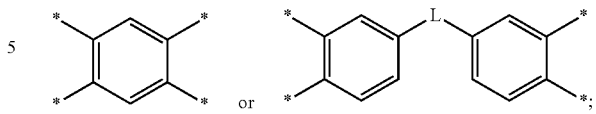

L may be —$CR^{c1}R^{c2}$—; $R^{c1}$ and $R^{c2}$ may be independently of each other $CH_3$ or $CF_3$; a and b may be independently of each other 0; and c and d may be independently of each other an integer of 1.

The polyimide precursor according to an exemplary embodiment may include a repeating unit represented by the following Chemical Formula F:

[Chemical Formula F]

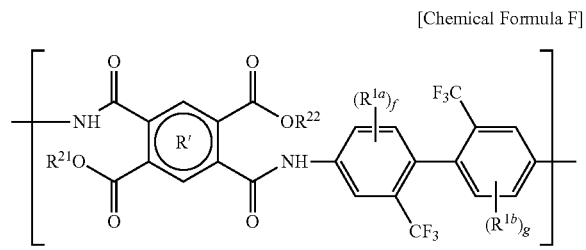

wherein

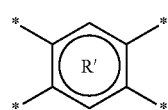

is as defined above for Chemical Formula D;

$R^{21}$ and $R^{22}$ are independently of each other hydrogen or C1-C10 alkyl;

$R^{1a}$ and $R^{1b}$ are independently of each other halogen, C1-C10 alkyl, haloC1-C10 alkyl, C1-C10 alkoxy, or C6-C12 aryl; and f and g are independently of each other an integer of 0 to 3.

In Chemical Formula F according to an exemplary embodiment,

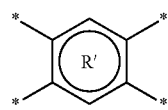

may be

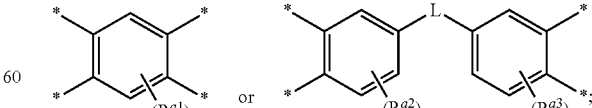

$R^{a1}$, $R^{a2}$, and $R^{a3}$ may be independently of one another C1-C5 alkyl or haloC1-C5 alkyl; $R^{21}$ and $R^{22}$ may be independently of each other hydrogen or C1-C5 alkyl; L may be a single bond, C1-C5 alkylene, —O—, —S—, —CO—, or —SO$_2$—, and the alkylene may be further substituted with one or more selected from C1-C5 alkyl and haloC1-C5 alkyl; $R^{1a}$ and $R^{1b}$ may be independently of each other halogen, C1-C5 alkyl, or haloC1-C5 alkyl; f and g may be independently of each other an integer of 0 or 1; and p, q, and r may be independently of one another an integer of 0 or 1.

Preferably, in Chemical Formula F according to an exemplary embodiment,

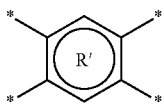

may be

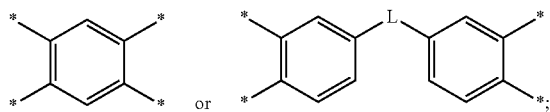

$R^{21}$ and $R^{22}$ may be independently of each other hydrogen; L may be a single bond or —$CR^{c1}R^{c2}$—; $R^{c1}$ and $R^{c2}$ may be independently of each other C1-C3 alkyl or haloC1-C3 alkyl, and more preferably $R^{c1}$ and $R^{c2}$ may be independently of each other CH$_3$ or CF$_3$; $R^{1a}$ and $R^{1b}$ may be independently of each other halogen, C1-C5 alkyl, or haloC1-C5 alkyl; and f and g may be independently of each other an integer of 0 or 1, and more preferably, f and g may be 0.

The polyimide precursor according to an exemplary embodiment essentially includes the repeating unit represented by Chemical Formula 11, and may further include the repeating unit represented by Chemical Formula F. Preferably, the polyimide precursor according to an exemplary embodiment essentially includes the repeating unit represented by Chemical Formula 12 or 13, and may further include the repeating unit represented by Chemical Formula F. More preferably, the polyimide precursor according to an exemplary embodiment essentially includes the repeating unit represented by Chemical Formula 12-1 or 13-1, and may further include the repeating unit represented by Chemical Formula F. More preferably, the polyimide precursor according to an exemplary embodiment essentially includes the repeating unit represented by Chemical Formula 12-2 or 13-2, and may further include the repeating unit represented by Chemical Formula F.

The polyimide precursor according to an exemplary embodiment may include 10 to 100 mol %, more preferably 30 to 100 mol %, favorably 40 to 95 mol %, and more favorably 50 to 80 mol % of the repeating unit represented by Chemical Formula 11.

The polyimide precursor according to an exemplary embodiment may include 90 mol % or less, 70 mol % or less, 5 to 60 mol %, or 20 to 50 mol % of the repeating unit represented by Chemical Formula F with respect to the total mol % of the polyimide precursor.

In addition, the present invention provides a polyimide-based polymer composition including the diamine compound having a structure according to the present invention.

The composition according to an exemplary embodiment may be a polyimide-based polymer composition including a structural unit derived from the diamine compound of Chemical Formula 1 and a structural unit derived from an acid dianhydride compound. The polyimide-based polymer composition includes both a polyimide and a polyimide precursor (that is, polyamic acid or polyamic acid ester).

The composition according to an exemplary embodiment may be a polyimide precursor composition including the polyimide precursor (that is, polyamic acid or polyamic acid ester) including the structural unit derived from the diamine compound of Chemical Formula 1 and the structural unit derived from the acid dianhydride compound, and an organic solvent.

In an exemplary embodiment, the polyimide precursor composition may be in the form of a solution of the polyimide precursor dissolved in an organic solvent. For example, when the polyimide precursor is synthesized in an organic solvent, the solution may be the reaction solution obtained itself, or diluted in another solvent. When the polyimide precursor is obtained as solid powder, this may be dissolved in an organic solvent to produce a solution.

In an exemplary embodiment, the polyimide precursor composition includes the polyimide precursor of the present invention described above, thereby implementing a polyimide film having significantly improved optical and mechanical properties.

In particular, the polyimide precursor composition of the present invention has high transparency and excellent heat resistance, and may provide a polyimide film having a low retardation.

The organic solvent in the polyimide precursor according to an exemplary embodiment may be, specifically, one or a mixture of two or more selected from ketones such as γ-butyrolactone, 1,3-dimethyl-2-imidazolidinone, methyl ethyl ketone, cyclohexanone, cyclopentanone, and 4-hydroxy-4-methyl-2-pentanone; aromatic hydrocarbons such as toluene, xylene, and tetramethylbenzene; glycolethers (cellosolve) such as ethyleneglycolmonoethylether, ethyleneglycolmonomethylether, ethyleneglycolmonobutylether, diethyleneglycolmonoethylether, diethyleneglycolmonomethylether, diethyleneglycolmonobutylether, propyleneglycolmonomethylether, propyleneglycolmonoethylether, dipropyleneglycoldiethylether, and triethyleneglycolmonoethylether; acetates such as ethyl acetate, butyl acetate, ethyleneglycolmonoethyletheracetate, ethyleneglycolmonobutyletheracetate, diethyleneglycolmonoethyletheracetate, and dipropyleneglycolmonomethyletheracetate; alcohols such as methanol, ethanol, propanol, ethyleneglycol, propyleneglycol, and carbitol; amides such as N,N-dimethylpropionamide (DMPA), N,N-diethylpropionamide (DEPA), N,N-dimethylacetamide (DMAc), N,N-diethylacetamide (DEAc), N,N-dimethylformamide (DMF), N,N-diethylformamide (DEF), N-methylpyrrolidone (NMP), N-ethylpyrrolidone (NEP), and N,N-dimethylmethoxyacetamide; and the like.

As an example, the organic solvent may be one or a mixture of two or more selected from the amides described above.

As an example, the organic solvent may be amides having a boiling point of 300° C. or lower, and specifically, may be N,N-diethylformamide (DEF), N,N-dimethylacetamide (DMAc), N,N-diethylacetamide (DEAc), N-ethylpyrrolidone (NEP), N,N-dimethylpropionamide (DMPA), N,N-diethylpropionamide (DEPA), or a combination thereof.

The polyimide precursor composition according to an exemplary embodiment may include a solid in an amount such that the composition has an appropriate viscosity considering the applicability in the process of forming a film, and the solid content may be 5 to 30 wt %, preferably 10 to 25 wt %, based on the total weight of the composition.

Specifically, the polyimide precursor composition according to an exemplary embodiment may satisfy a viscosity of 2,000 to 50,000 cps. The viscosity may satisfy, specifically, 30,000 cps or less. When the viscosity range as such is satisfied, defoaming efficiency in processing of the polyimide film is excellent to provide an advantage in the process. Thus, a more uniform surface may be implemented. Here, the viscosity refers to a value measured using a Brookfield RVDV-III viscometer spindle No. 52, after placing a sample at room temperature (25° C.), and subjecting the sample to a stabilization operation for 2 minutes when a torque value is at 80%.

The polyimide precursor composition according to an exemplary embodiment may be prepared by polymerization of the diamine compound according to an exemplary embodiment and the acid dianhydride compound in the presence of an organic solvent, and the diamine compound according to an exemplary embodiment and the acid dianhydride may be polymerized at a mole ratio of 2:1 to 1:2, preferably 1.5:1 to 1:1.5, and more preferably 1:1.1 to 1.1:1. The mole ratio may be changed depending on intended reactivity and processability.

The polymerization of the diamine compound according to an exemplary embodiment and the acid dianhydride may be performed at a temperature of 70° C. or lower, 10 to 70° C., or 20 to 30° C. under inert gas or nitrogen stream.

A molecular weight of the polyimide precursor according to an exemplary embodiment is not particularly limited, but as an example, when the weight average molecular weight (in terms of polystyrene) is in a range of 20,000 to 150,000 g/mol, a polyimide film having better physical properties may be obtained.

The polyimide precursor composition according to an exemplary embodiment may further include an additive such as a leveling agent, a retardant, an adhesion improver, inorganic particles, an antioxidant, a UV protection agent, and a plasticizer.

In addition, the present invention provides a method of manufacturing a polyimide film, and specifically, the polyimide film according to the present invention may be manufactured by applying the polyimide precursor composition on a substrate; and performing a heat treatment to form a polyimide film.

The polyimide is a polyimide having a cyclic chemical structure (—CO—N—CO—) obtained by imidizing the polyimide precursor to dehydrate H of —CO—NH— and OH of —CO—OH in the polyimide precursor.

The imidization may be performed by a chemical imidization or thermal imidization method. For example, the polyimide may be obtained by a method of adding a dehydrating agent and an imidization catalyst to the polymerized polyimide precursor composition and heating the mixture to a temperature of 50 to 120° C. to perform imidization by a chemical reaction, or removing alcohol while refluxing the solution to perform imidization.

The imidization according to an exemplary embodiment may be through a chemical imidization method.

In the chemical imidization method, as the imidization catalyst, pyridine, triethylamine, picoline, quinoline, or the like may be used, and also, substituted or unsubstituted nitrogen-containing heterocyclic compounds, N-oxide compounds of nitrogen-containing heterocyclic compounds, substituted or unsubstituted amino acid compounds, aromatic hydrocarbon compounds having a hydroxyl group, or aromatic heterocyclic compounds may be used, and in particular, lower alkylimidazole such as 1,2-dimethylimidazole, N-methylimidazole, N-benzyl-2-methylimidazole, 2-methylimidazole, 2-ethyl-4-methylimidazole, and 5-methylbenzimidazole, substituted pyridine such as isoquinoline, 3,5-dimethylpyridine, 3,4-dimethylpyridine, 2,5-dimethylpyridine, 2,4-dimethylpyridine, and 4-n-propylpyridine, p-toluenesulfonic acid, or the like may be used. The imidization catalyst may be used at a content of 0.1 to 5 mol with respect to 1 mol of the acid dianhydride.

As the dehydrating agent, acid anhydrides or acid chlorides thereof such as anhydrous acetic acid, anhydrous propionic acid, and anhydrous benzoic acid; carbodiimide compounds such as dicyclohexyl dicarbodiimide; or the like may be used. The dehydrating agent may be used at a content of 0.1 to 10 mol with respect to 1 mol of the acid dianhydride.

In the chemical imidization, a heating process at a temperature of 50 to 120° C. may be performed together.

The imidization according to an exemplary embodiment may be through a thermal imidization method. The imidization may be performed by a method of applying the polyimide precursor composition on a substrate and then performing a heat treatment.

More specifically, the polyimide film according to the present invention may be manufactured by imidizing the polyimide precursor composition to prepare a polyimide-based polymer composition; and applying the polyimide-based polymer composition on a substrate and then performing a heat treatment (curing), in which the imidization may be applied by the chemical imidization described above or a combination of the chemical imidization and thermal imidization.

In addition, the polyimide film according to the present invention may be manufactured by a manufacturing method including applying the polyimide precursor composition on a substrate and then performing a heat treatment (curing), in which as the imidization, the thermal imidization described above may be applied.

The substrate according to an exemplary embodiment may be a glass substrate, a metal substrate, a plastic substrate, and the like, without particular limitation. Among them, a glass substrate is preferred, since it has excellent thermal and chemical stability during imidization and curing process to the polyimide precursor composition, and a polyimide film formed after curing may be easily separated therefrom without damage.

Specifically, the method for application and coating according to an exemplary embodiment is not particularly limited, but as an example, any one or more methods selected from spin coating, dipping, spraying, die coating, bar coating, roll coating, meniscus coating, flexo printing, screen printing, bead coating, airknife coating, reversroll coating, blade coating, casting coating, gravure coating, and the like may be used.

In an exemplary embodiment, the polyimide precursor composition or the polyimide-based polymer composition may be applied on a substrate in a thickness range such that the finally manufactured polyimide film has an appropriate thickness for a display substrate. Specifically, the composition may be applied in an amount to be a thickness of 10 to 100 μm, but is not limited thereto, and may be adjusted depending on the purpose.

The heat treatment according to an exemplary embodiment may be performed at 500° C. or lower, preferably 80 to 500° C., and more preferably 80 to 300° C.

The heat treatment according to an exemplary embodiment may proceed in a total of 3 steps, and may include a first heat treatment step performed at 100° C. or lower, specifically 80 to 100° C.; a second heat treatment step performed at higher than 100° C. and 300° C. or lower; and a third heat treatment step performed at higher than 300° C. and 500° C. or lower, but is not limited thereto.

In an exemplary embodiment, before the heat treatment (curing) step, a drying step for removing an organic solvent present in the polyimide precursor composition may be further included. The drying step may be performed according to a common method, and may be performed at a temperature of, specifically 140° C. or lower, preferably 80° C. to 140° C.

In an exemplary embodiment, after the heat treatment (curing) step, a separation step from the substrate may be further included.

In addition, the present invention provides a polyimide film manufactured using the polyimide precursor according to an exemplary embodiment, and the polyimide film of the present invention includes a repeating unit represented by the following Chemical Formula 14:

[Chemical Formula 14]

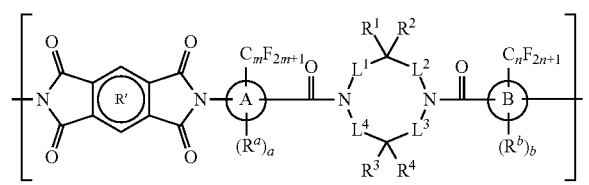

wherein

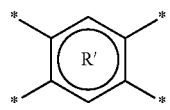

is as defined above for Chemical Formula D;

$L^1$ to $L^4$ are independently of one another a single bond or C1-C10 alkylene;

$R^1$ to $R^4$ are independently of one another hydrogen, halogen, C1-C10 alkyl, haloC1-C10 alkyl, C1-C10 alkoxy, C3-C10 cycloalkyl, or C6-C20 aryl, or $R^1$ and $R^3$ may be linked to each other by —NR'—, —O—, or —S— to form a ring;

R' is hydrogen, C1-C10 alkyl, C3-C10 cycloalkyl, or C6-C20 aryl;

ring A and ring B are independently of each other a C6-C20 aromatic ring;

$R^a$ and $R^b$ are independently of each other halogen, C1-C10 alkyl, haloC1-C10 alkyl, C1-C10 alkoxy, C3-C10 cycloalkyl, or C6-C20 aryl;

a and b are independently of each other an integer of 0 to 3; and m and n are independently of each other an integer of 1 to 10.

In Chemical Formula 14 according to an exemplary embodiment, ring A and ring B may be independently of each other benzene or naphthalene;

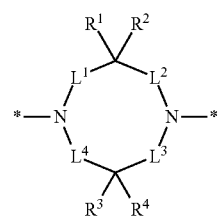

may be

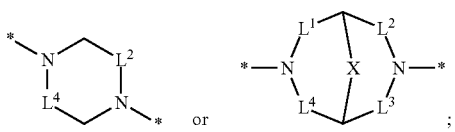

$L^1$ to $L^4$ may be independently of each other C1-C5 alkylene; X may be —NR'—, —O—, or —S—; R' may be hydrogen or C1-C5 alkyl; $R^a$ and $R^b$ may be independently of each other halogen, C1-C5 alkyl, haloC1-C5 alkyl, C1-C5 alkoxy, C3-C7 cycloalkyl, or C6-C12 aryl;

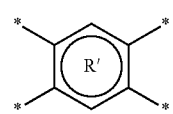

may be

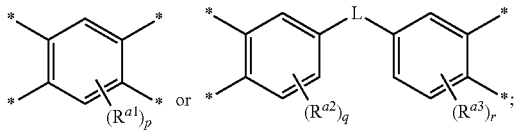

$R^{a1}$, $R^{a2}$, and $R^{a3}$ may be independently of one another C1-C5 alkyl or haloC1-C5 alkyl; L may be a single bond, C1-C5 alkylene, —O—, —S—, —CO—, or —SO$_2$—, and the alkylene may be further substituted with one or more selected from C1-C5 alkyl and haloC1-C5 alkyl; a and b may be independently of each other an integer of 0 or 1; m and n may be independently of each other an integer of 1 to 5; and p, q, r may be independently of one another an integer of 0 or 1.

The polyimide film according to an exemplary embodiment may include a repeating unit represented by the following Chemical Formula 15 or 16:

[Chemical Formula 15]

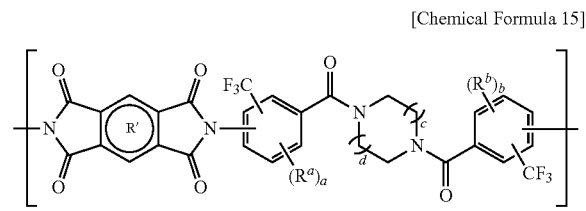

-continued

[Chemical Formula 16]

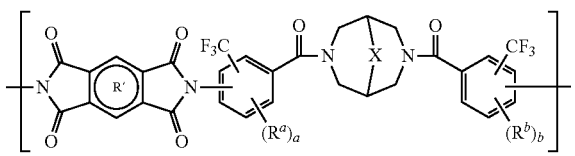

wherein

X is —O— or —S—;

$R^a$ and $R^b$ are independently of each other halogen, C1-C5 alkyl, or haloC1-C5 alkyl;

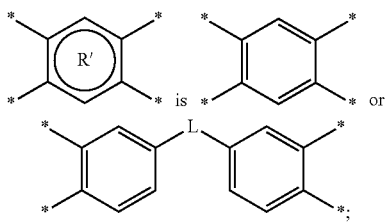

L is a single bond or —$CR^{c1}R^{c2}$—;

$R^{c1}$ and $R^{c2}$ are independently of each other C1-C3 alkyl or haloC1-C3 alkyl;

a and b are independently of each other an integer of 0 or 1; and c and d are independently of each other an integer of 1 or 2.

The polyimide film according to an exemplary embodiment may include a repeating unit represented by the following Chemical Formula 15-1 or 16-1:

[Chemical Formula 15-1]

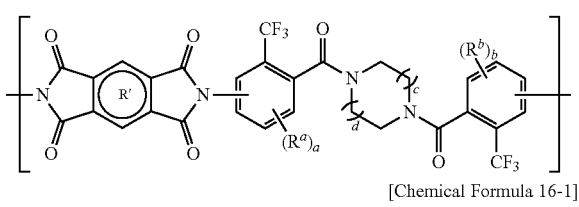

[Chemical Formula 16-1]

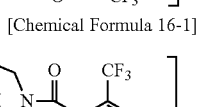

wherein

X is —O— or —S—;

$R^a$ and $R^b$ are independently of each other halogen, C1-C5 alkyl, or haloC1-C5 alkyl;

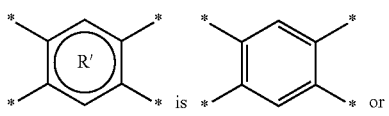

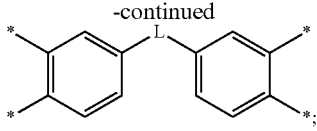

L is a single bond or —$CR^{c1}$—$R^{c2}$—;

$R^{c1}$ and $R^{c2}$ are independently of each other C1-C3 alkyl or haloC1-C3 alkyl;

a and b are independently of each other an integer of 0 or 1; and c and d are independently of each other an integer of 1 or 2.

Preferably, the polyimide film according to an exemplary embodiment may include a repeating unit represented by the following Chemical formula 15-2 or 16-2:

[Chemical Formula 15-2]

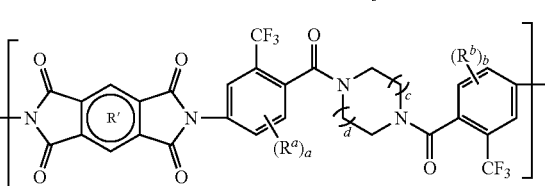

[Chemical Formula 16-2]

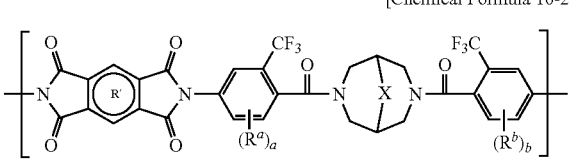

wherein

X is —O— or —S—;

$R^a$ and $R^b$ are independently of each other halogen or haloC1-C5 alkyl;

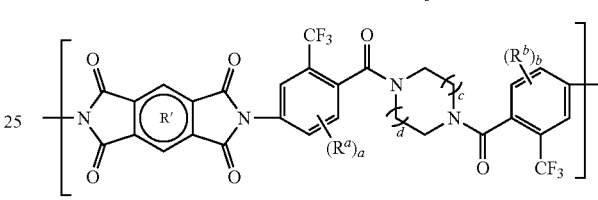
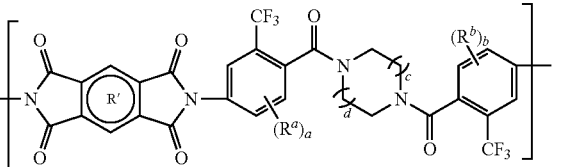

L is a single bond or —$CR^{c1}R^{c2}$—;

$R^{c1}$ and $R^{c2}$ are independently of each other C1-C3 alkyl or haloC1-C3 alkyl;

a and b are independently of each other an integer of 0 or 1; and c and d are independently of each other an integer of 1 or 2.

Specifically, in Chemical Formulae 15 and 16 according to an exemplary embodiment, X may be —O—.

Specifically, in Chemical Formulae 15 and 16 according to an exemplary embodiment, c and d may be independently of each other an integer of 1.

Specifically, in Chemical Formulae 15 and 16 according to an exemplary embodiment, a and b may be independently of each other 0.

Specifically, in Chemical Formulae 15 and 16 according to an exemplary embodiment,

[benzene ring with R' substituent and four * positions]

may be

[benzene ring with four * positions] or [two benzene rings connected by L with four * positions];

L may be —$CR^{c1}R^{c2}$—; and $R^{c1}$ and $R^{c2}$ may be independently of each other $CH_3$ or $CF_3$.

More specifically, in Chemical Formulae 15 and 16 according to an exemplary embodiment, X may be —O—;

[benzene ring with R' substituent]

may be

[benzene ring] or [two benzene rings connected by L];

L may be —$CR^{c1}R^{c2}$—; $R^{c1}$ and $R^{c2}$ may be independently of each other $CH_3$ or $CF_3$; a and b may be independently of each other 0; and c and d may be independently of each other an integer of 1.

The polyimide film according to an exemplary embodiment may further include a repeating unit represented by the following Chemical Formula G:

[Chemical Formula G]

[Structure showing a polymer repeating unit with two imide groups attached to a benzene ring with R' substituent, connected via N to a biphenyl system with $CF_3$ groups and $(R^{1a})_f$ and $(R^{1b})_g$ substituents]

wherein

[benzene ring with R' substituent and four * positions]

is as defined above for Chemical Formula D;

$R^{1a}$ and $R^{1b}$ are independently of each other halogen, C1-C10 alkyl, haloC1-C10 alkyl, C1-C10 alkoxy, or C6-C12 aryl; and f and g are independently of each other an integer of 0 to 3.

In Chemical Formula G according to an exemplary embodiment,

[benzene ring with R' substituent]

may be

[benzene ring with $(R^{a1})_p$ substituent] or [two benzene rings connected by L with $(R^{a2})_q$ and $(R^{a3})_r$ substituents];

$R^{a1}$, $R^{a2}$, and $R^{a3}$ may be independently of one another C1-C5 alkyl or haloC1-C5 alkyl; L may be a single bond, C1-C5 alkylene, —O—, —S—, —CO—, or —$SO_2$—, and the alkylene may be further substituted with one or more selected from C1-C5 alkyl and haloC1-C5 alkyl; Ria and Rib may be independently of each other halogen, C1-C5 alkyl, or haloC1-C5 alkyl; f and g may be independently of each other an integer of 0 or 1; and p, q, and r may be independently of one another an integer of 0 or 1.

Preferably, in Chemical Formula G according to an exemplary embodiment,

[benzene ring with R' substituent]

may be

[benzene ring] or [two benzene rings connected by L];

L may be a single bond or —$CR^{c1}R^{c2}$—; $R^{c1}$ and $R^{c2}$ may be independently of each other C1-C3 alkyl or haloC1-C3 alkyl, and more preferably $R^{c1}$ and $R^{c2}$ may be independently of each other $CH_3$ or $CF_3$; $R^{1a}$ and $R^{1b}$ may be independently of each other halogen, C1-C5 alkyl, or haloC1-C5 alkyl; and f and g may be independently of each other an integer of 0 or 1, and more preferably, f and g may be 0.

The polyimide film according to an exemplary embodiment essentially includes the repeating unit represented by Chemical Formula 14, and may further include the repeating unit represented by Chemical Formula G. Preferably, the polyimide film according to an exemplary embodiment essentially includes the repeating unit represented by Chemical Formula 15 or 16, and may further include the repeating unit represented by Chemical Formula G. More preferably, the polyimide film according to an exemplary embodiment essentially includes the repeating unit represented by Chemical Formula 15-1 or 16-1, and may further include the repeating unit represented by Chemical Formula G. More preferably, the polyimide film according to an exemplary embodiment essentially includes the repeating unit represented by Chemical Formula 15-2 or 16-2, and may further include the repeating unit represented by Chemical Formula G.

The polyimide according to an exemplary embodiment may include 10 to 100 mol %, more preferably 30 to 100 mol %, favorably 40 to 95 mol %, and more favorably 50 to 80 mol % of the repeating unit represented by Chemical Formula 14.

The polyimide according to an exemplary embodiment may include 90 mol % or less, 70 mol % or less, 5 to 60 mol %, or 20 to 50 mol % of the repeating unit represented by Chemical Formula G with respect to the total mol % of the polyimide precursor.

The weight average molecular weight (in terms of polystyrene) of the polyimide film according to an exemplary embodiment, that is, polyimide, may be 10,000 to 200,000 g/mol, 20,000 to 100,000 g/mol, or 30,000 to 100,000 g/mol. In addition, the molecular weight distribution (Mw/Mn) of the polyimide according to the present invention may satisfy a range of 1.1 to 2.5. When the weight average molecular weight and the molecular weight distribution of the polyimide described above are satisfied, it is favorable to the characteristics of the polyimide film such as optical properties, heat resistance, mechanical strength, and flexibility.

The polyimide film according to an exemplary embodiment includes the structural unit derived from the diamine compound of Chemical Formula 1, thereby showing more improved retardation properties, with excellent transmittance, high heat resistance, and mechanical strength.

Specifically, the polyimide film according to an exemplary embodiment may have a retardation value in the thickness direction ($R_{th}$) of 1500 nm or less, preferably 500 to 1400 nm, and more preferably 1000 to 1350 nm, at a thickness of 50 μm. In the range of the retardation in the thickness direction, appropriate viewing sensibility for a display may be expressed. When the retardation in the thickness direction is more than 1500 nm, retardation occurs in the polyimide film, so that light looks distorted to significantly deteriorate the viewing sensibility.

The polyimide film according to an exemplary embodiment is a colorless and transparent polyimide film, and may have a total light transmittance to the light at a wavelength of 380 to 760 nm of 80% or more, preferably 90% or more in the thickness range of the film of 10 to 50 μm, a yellow index (YI) in accordance with ASTM E313 of 10 or less, preferably 5 or less, and more preferably 2 to 5, and a Young's modulus in accordance with ASTM D882 of 3 to 4 GPa.

In addition, the polyimide film according to the present invention may have excellent thermal stability with a temperature change.

That is, the polyimide film according to the present invention is manufactured using the diamine compound having a specific structure as a monomer, thereby having excellent optical properties and mechanical properties as described above. Specifically, since the polyimide film includes the repeating unit derived from the diamine compound of Chemical Formula 1, it has excellent optical properties, heat resistance, mechanical strength, and flexibility, and in particular, a highly transparent polyimide film having low retardation properties may be provided. Therefore, the polyimide film of the present invention may be used in various fields such as a substrate for a device, a cover substrate for a display, an optical film, an integrated circuit (IC) package, a deposition film, a multilayer flexible printed circuit (FPC), a tape, a touch panel, and a protective film for an optical disc.

The polyimide film according to an exemplary embodiment may be used as a laminate which is in the form of being laminated in two or more layers.

In addition, the present invention provides a photoelectric device and a flexible display which include the polyimide film or the laminate in which the films are laminated as a flexible substrate.

As an example, the photoelectric device may include an optical component, a switch, a light modulator, and the like, and simultaneously, the present invention is appropriate for a heat-resistant substrate material requiring micropattern formation properties.

As an example, the flexible display may include a liquid crystal display device (LCD), an organic light emitting diode (OLED), and the like, and in particular, may be appropriate for an OLED device using a low temperature polysilicon (LTPS) process requiring a high temperature process, but the present invention is not limited thereto.

Hereinafter, the present invention will be described by the specific examples and the comparative examples of the present invention. The following examples are for illustrating the technical spirit of the present invention, and it is apparent to a person skilled in the art that the present invention is not limited to the examples.

[Evaluation Method]

1. Film thickness: 0.5 T glass was coated with PAA, and then the thickness of the cured substrate was measured using a film thickness measuring instrument (Alpha step D500) available from KLA Corporation. The unit is μm.

2. Viscosity: refers to a value measured using a Brookfield RVDV-III viscometer spindle No. 52, after placing a sample at room temperature (25° C.), and allowing the sample to stand for 2 minutes and stabilizing the same when a torque value is at 80%. The unit is cps.

3. Retardation (converted value at a thickness of 50 μm): after a retardation in the thickness direction ($R_{th}$) was measured using a retardation measuring instrument (manufactured by Axometrics Inc., Axoscan, measurement wavelength: 550 nm), the determined retardation measurement value in the thickness direction (measurement value by automatic measurement using a measuring instrument) was used to convert the value into a retardation value per a thickness of 50 μm of the film. The unit is nm. In addition, a refractive index which is a basic data of the retardation measuring instrument was measured by Abbe refractometer (manufactured by ATAGO CO., LTD., NAR-4T, measurement wave length: 589.3 nm).

4. Total light transmittance: measured throughout the wavelength region from 380 nm to 780 nm using a spectrophotometer (Shimadzu Corporation, MPC-3100) in accordance with the ASTM D1746 specification. The unit is %.

5. Yellow index (YI): measured using a colorimeter (HunterLab, ColorQuest XE) in accordance with the ASTM E313 specification.

6. Young's modulus: measured using Instron UTM 3365 under the condition of pulling a polyimide film having a length of 40 mm and a width of 5 mm at 10 mm/min at 25° C. in accordance with ASTM D882. The modulus unit is GPa.

[Preparation Example 1] Preparation of Diamine Compound (1)

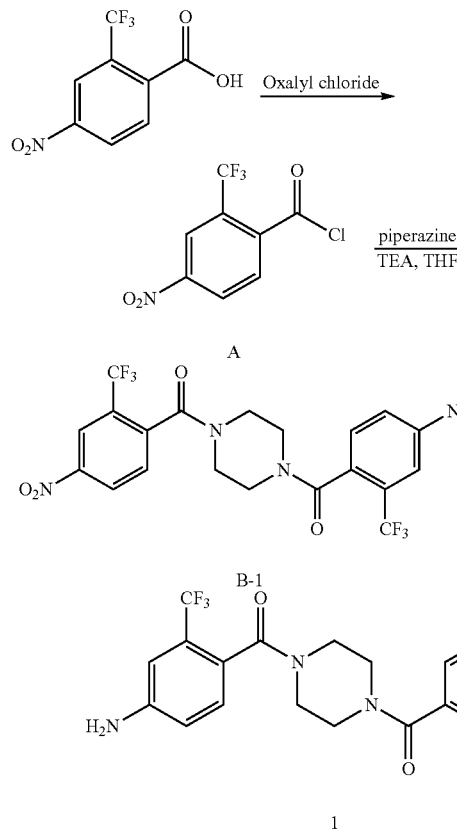

Step 1. Preparation of Compound (A)

4-nitro-2-trifluoromethyl benzoic acid (20 g) was added to DCM (200 mL) under a nitrogen environment and then the solution was cooled to 0° C. Oxalyl chloride (16 g) was slowly added thereto to perform a reaction for 1 hour, and then DMF (1 g) was added thereto. Stirring was performed at room temperature for 6 hours, and the solvent was removed by reduced pressure distillation to obtain compound (A) (4-nitro-2-trifluoromethyl benzoylchloride) (22 g).

Step 2. Preparation of Compound (B-1)

Compound (A) (11 g) obtained in step 1 and TEA (5 g) were dissolved in THF (100 mL) and then cooled to 0° C. Piperazine (1.8 g) dissolved in THF (20 mL) was slowly added thereto to perform a reaction for 1 hour, and then the temperature was raised to room temperature. Stirring was performed for 12 hours, distilled water (50 mL) was added thereto, and THF was removed with reduced pressure distillation. The solid obtained after filtering was washed with distilled water (50 mL) and dried to obtain compound (B-1) as a pale yellow solid (10 g, yield: 90%).

Step 3. Preparation of Diamine Compound (1)

Compound (B-1) (10 g) obtained in step 2 was added to MeOH (100 mL), and then 10% Pd/C (1 g) was added thereto. $H_2$ was bubbled, stirring was performed for 6 hours, filtration was performed to remove the catalyst, and the solvent was removed with reduced pressure distillation. Reslurrying was performed with MeOH to obtain a diamine compound (1) (5.6 g, yield: 63%) as a pale yellow solid.

$^1$H NMR (DMSO-$d_6$, 500 MHz, ppm): 7.06 (d, 2H), 6.88 (d, 2H, J=18.5 Hz), 6.77 (d, 2H, J=18.5 Hz), 5.80 (d, 1H, J=18 Hz), 3.61 (d, 4H, J=22.5 Hz), 3.12 (d, 4H, J=22.5 Hz).

[Preparation Example 2] Preparation of Diamine Compound 2

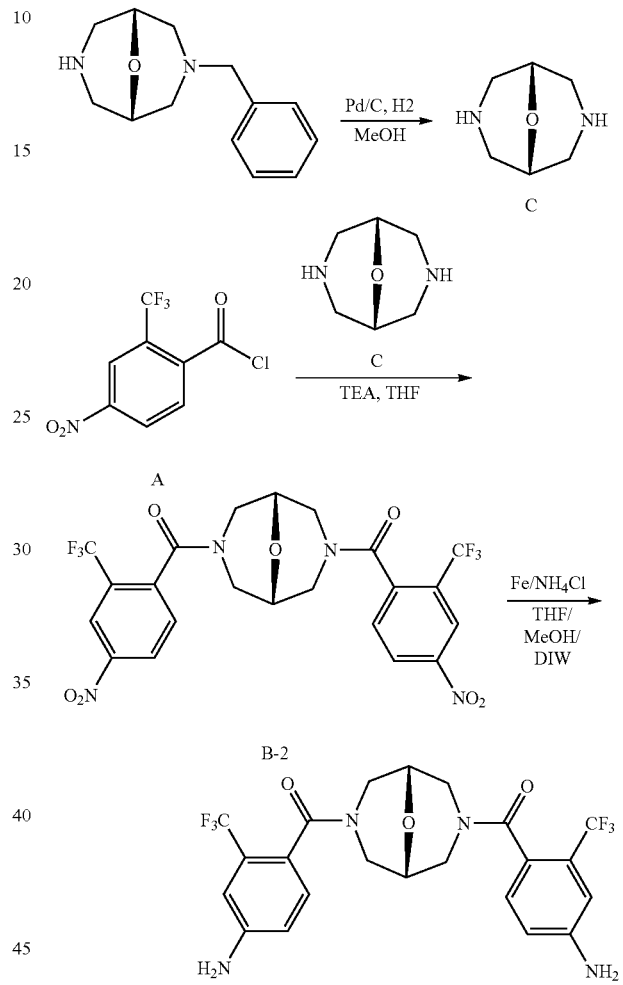

Step 1. Preparation of Compound C

3-Benzyl-9-oxa-3,7-diazabicyclo[3.3.1]nonane dihydrochloride as a starting material was prepared by referring to KR 10-2008-0017410 A.

The starting material (10 g) was added to MeOH (100 mL), and then 10% Pd/C (1 g) was added thereto. $H_2$ was bubbled, stirring was performed for 6 hours, filtration was performed to remove the catalyst, and the solvent was removed with reduced pressure distillation to obtain compound C (9-oxabispidine) (4 g, yield: 68%).

Step 2. Preparation of Compound (B-2)

Compound (A) (11 g) and TEA (5 g) were dissolved in THF (100 mL) in a separate reactor, and then cooled to 0° C. Compound C (9-oxabispidine) (2.8 g) was dissolved in THF (20 mL), slowly added, and reacted for 1 hour, and the temperature was raised to room temperature. Stirring was performed for 12 hours, distilled water (50 mL) was added thereto, and THF was removed with reduced pressure distillation. The solid obtained after filtering was washed with distilled water (50 mL) and dried to obtain compound (B-2) as a pale yellow solid (11.8 g, yield: 90%).

Step 3. Preparation of Diamine Compound 2

Compound (B-2) (11.8 g) obtained in step 2 was dissolved in THF (60 ml), MeOH (60 ml), and distilled water (60 ml), and 9.4 g of Fe powder and 9.0 g of $NH_4Cl$ were added at room temperature. The temperature was raised to 60° C. and stirring was performed for 24 hours. A solid material present in a reaction solution was filtered through a celite pad using EA (100 ml), and distilled water (100 ml) was added to separate layers and remove an aqueous layer. Thereafter, an organic layer was washed once with distilled water (100 ml), the organic layer was dried with magnesium sulfate, and a solid was filtered. The organic layer was concentrated under reduced pressure until a solid was precipitated, reslurrying was performed with MeOH to obtain a diamine compound 2 (7.2 g, yield: 68%) as a pale yellow solid.

$^1$H NMR (Methanol-$d_4$, 500 MHz, ppm): 7.24 (d, 2H, J=7 Hz), 6.99 (s, 2H), 6.91 (d, 2H, J=7 Hz), 4.60 (s, 2H), 4.48 (d, 2H, J=13.5 Hz), 3.99 (s, 2H), 3.57 (d, 2H, J=12.5 Hz), 3.46 (d, 2H, J=12.5 Hz), 3.26 (m, 4H).

[Example 1] Preparation of Polyimide Precursor Solution

6FDA/(TFMB/Diamine Compound (1)) (Mole Ratio: 1/(0.9/0.1))

A reactor in which a nitrogen stream flowed was filled with N,N-dimethylacetamide (DMAc) (33.797 g), and TFMB (2,2'-bis(trifluoromethyl)-4,4'-biphenyl diamine) (5.332 g) and diamine compound (1) (0.852 g) were dissolved therein while the temperature of the reactor was maintained at 25° C. 4,4'-(hexafluoroisopropylidene)diphthalic anhydride (6FDA) (8.301 g) was added to the solution of TFMB/diamine compound (1) at the same temperature, sufficient stirring was performed, and polymerization was performed at 40° C. for 18 hours. At this time, the solid content was 30%. Subsequently, pyridine (3.695 g) and acetic acid anhydride (4.769 g) were sequentially introduced to the solution as a catalyst and a dehydrating agent, and stirring was performed at 60° C. for 24 hours to prepare a polyimide-based polymer solution. The polyimide-based polymer solution prepared had a viscosity of 27,580 cPs and a final solid content of 21.2 wt %.

[Example 2] Preparation of Polyimide Precursor Solution

6FDA/(TFMB/Diamine Compound (1)) (Mole Ratio: 1/(0.7/0.3))

A reactor in which a nitrogen stream flowed was filled with DMAc (64.693 g), and TFMB (5.044 g) and diamine compound (1) (3.108 g) were dissolved in a state in which the temperature of the reactor was maintained at 25° C. 6FDA (10.095 g) was added to the solution of TFMB/diamine compound (1) at the same temperature, sufficient stirring was performed, and polymerization was performed at 40° C. for 18 hours. At this time, the solid content was 22%. Subsequently, pyridine (4.494 g) and acetic acid anhydride (5.800 g) were sequentially introduced to the solution as a catalyst and a dehydrating agent, and stirring was performed at 60° C. for 24 hours to prepare a polyimide-based polymer solution. The polyimide-based polymer solution prepared had a viscosity of 5,606 cPs and a final solid content of 16.8 wt %.

[Example 3] Preparation of Polyimide Precursor Solution

6FDA/(TFMB/Diamine Compound 2) (Mole Ratio: 1/(0.9/0.1))

A reactor in which a nitrogen stream flowed was filled with DMAc (51.629 g), and TFMB (5.332 g) and diamine compound 2 (0.930 g) were dissolved in a state in which the temperature of the reactor was maintained at 25° C. 6FDA (8.301 g) was added to the solution of TFMB/diamine compound 2 at the same temperature, sufficient stirring was performed, and polymerization was performed at 40° C. for 18 hours. At this time, the solid content was 22%. Subsequently, pyridine (3.695 g) and acetic acid anhydride (4.769 g) were sequentially introduced to the solution as a catalyst and a dehydrating agent, and stirring was performed at 60° C. for 24 hours to prepare a polyimide-based polymer solution. The polyimide-based polymer solution prepared had a viscosity of 2,090 cPs and a final solid content of 18.6 wt %.

[Comparative Example 1] Preparation of Polyimide Precursor Solution

6FDA/TFMB (Mole Ratio: 1/1)

A reactor in which a nitrogen stream flowed was filled with DMAc (63.793 g), and TFMB (7.494 g) was dissolved in a state in which the temperature of the reactor was maintained at 25° C. 6FDA (10.499 g) was added to the solution at the same temperature, sufficient stirring was performed, and polymerization was performed at 40° C. for 18 hours. At this time, the solid content was 22%. Subsequently, pyridine (4.674 g) and acetic acid anhydride (6.032 g) were sequentially introduced to the solution as a catalyst and a dehydrating agent, and stirring was performed at 60° C. for 24 hours to prepare a polyimide-based polymer solution. The polyimide-based polymer solution prepared had a viscosity of 15,480 cPs and a final solid content of 16.6 wt %.

[Experimental Example 1] Manufacture of Polyimide Film

The polyimide-based polymer solutions prepared in Examples 1 to 3 and Comparative Example 1 were applied on a glass plate in a manner of spreading thinly, and then dried at 90° C. for 20 minutes. Subsequently, the dried film was peeled off from the glass plate support, the base film was fixed using a pin tenter, and heat treated for 1 hour in a state of heating up to 280° C. at a heating rate of 10° C./min to manufacture a polyimide film.

The physical properties of the polyimide films manufactured by the above method were evaluated by the above evaluation methods, and the results are shown in the following Table 1.

TABLE 1

|  | Example 1 | Example 2 | Example 3 | Comparative Example 1 |
|---|---|---|---|---|
| Thickness (μm) | 45 | 54 | 46 | 60 |
| Retardation (converted value at a thickness of 50 μm) (nm) | 1308 | 1046 | 1318 | 1568 |
| Total light transmittance (380-780 nm) (%) | 91.9 | 91.2 | 91.1 | 91.2 |
| YI (yellow index) | 2.29 | 4.37 | 3.31 | 1.8 |
| Young's modulus (GPa) | 3.9 | 3.7 | 3.9 | 3.8 |

As seen in the above Table 1, it was confirmed that the polyimide films obtained in Examples 1 to 3 showed significantly lower retardation values than that of Comparative Example 1, and showed other optical and mechanical properties at an excellent level.

That is, it was confirmed that the polyimide films of Examples 1 to 3 included a structural unit derived from a diamine compound having a structure in which an aromatic ring to which a fluoro-substituted alkyl group and an amino group are introduced is connected to a nitrogen atom-containing ring having a specific structure by an amide bond, unlike Comparative Example 1, thereby implementing low retardation properties showing a low retardation in the thickness direction.

Therefore, a low retardation polyimide film showing excellent optical properties, in particular, a low retardation in the thickness direction may be manufactured from the diamine compound having a specific structure according to the present invention.

According to the present invention, a diamine compound for synthesizing a polyimide which may implement excellent transparency and a low retardation may be provided.

The diamine compound having a structure according to the present invention has a structure in which an aromatic ring to which a fluoro-substituted alkyl group and an amino group are introduced is connected to a nitrogen atom-containing ring having a specific structure by an amide bond, and may be used as a monomer to manufacture a highly transparent polyimide film having improved physical properties, in particular, retardation improvement properties.

A structural unit derived from the diamine compound having a structure according to the present invention is included in a polyimide, thereby significantly decreasing a retardation in the thickness direction of a film.

That is, the polyimide film according to the present invention includes a structural unit derived from the diamine compound having a structure, thereby having excellent transparency and flexibility and also having low retardation properties to show a low retardation in the thickness direction.

Therefore, the polyimide film according to the present invention has excellent transparency and heat resistance, and also, may be very useful in various fields such as a substrate for a device, a substrate for a flexible display, an optical film, an integrated circuit (IC) package, an adhesive film, a multilayer flexible printed circuit (FPC), a tape, a touch panel, and a protective film for an optical disc.

Hereinabove, although the present invention has been described by specified matters and specific exemplary embodiments, they have been provided only for assisting in the entire understanding of the present invention. Therefore, the present invention is not by the specific matters limited to the exemplary embodiments. Various modifications and changes may be made by those skilled in the art to which the present invention pertains from this description.

Therefore, the spirit of the present invention should not be limited to the above-described exemplary embodiments, and the following claims as well as all modified equally or equivalently to the claims are intended to fall within the scope and spirit of the invention.

What is claimed is:

1. A diamine compound represented by the following Chemical Formula 1:

[Chemical Formula 1]

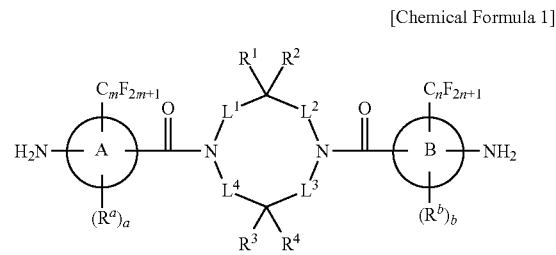

wherein $L^1$ to $L^4$ are independently of one another a single bond or C1-C10 alkylene;

$R^1$ to $R^4$ are independently of one another hydrogen, halogen, C1-C10 alkyl, haloC1-C10 alkyl, C1-C10 alkoxy, C3-C10 cycloalkyl, or C6-C20 aryl, or $R^1$ and $R^3$ may be linked to each other by —NR'—, —O—, or —S— to form a ring;

R' is hydrogen, C1-C10 alkyl, C3-C10 cycloalkyl, or C6-C20 aryl;

ring A and ring B are independently of each other a C6-C20 aromatic ring;

$R^a$ and $R^b$ are independently of each other halogen, C1-C10 alkyl, haloC1-C10 alkyl, C1-C10 alkoxy, C3-C10 cycloalkyl, or C6-C20 aryl;

a and b are independently of each other an integer of 0 to 3; and m and n are independently of each other an integer of 1 to 10.

2. The diamine compound of claim 1, wherein $L^1$ and $L^3$ are independently of each other a single bond or C1-C5 alkylene; $L^2$ and $L^4$ are independently of each other C1-C5 alkylene; and ring A and ring B are independently of each other benzene or naphthalene.

3. The diamine compound of claim 2, wherein the diamine compound is represented by the following Chemical Formula 2 or 3:

[Chemical Formula 2]

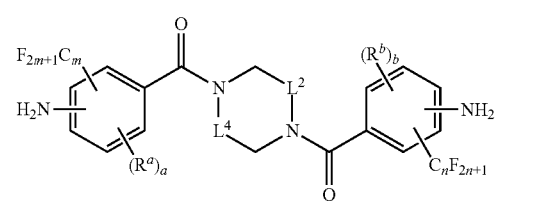

[Chemical Formula 3]

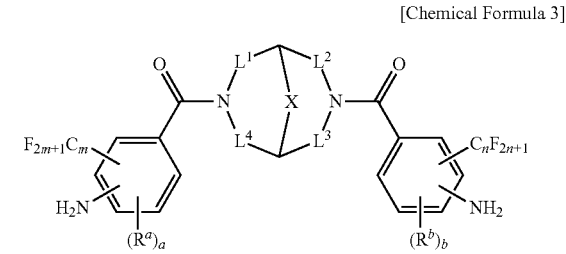

wherein

L¹ to L⁴ are independently of one another C1-C5 alkylene;

X is —NR'—, —O—, or —S—;

R' is hydrogen or C1-C5 alkyl;

$R^a$ and $R^b$ are independently of each other halogen, C1-C5 alkyl, haloC1-C5 alkyl, C1-C5 alkoxy, C3-C7 cycloalkyl, or C6-C12 aryl;

a and b are independently of each other an integer of 0 or 1; and m and n are independently of each other an integer of 1 to 5.

4. The diamine compound of claim 3, wherein the diamine compound is represented by the following Chemical Formula 4 or 5:

[Chemical Formula 4]

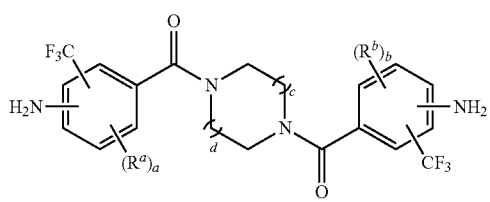

[Chemical Formula 5]

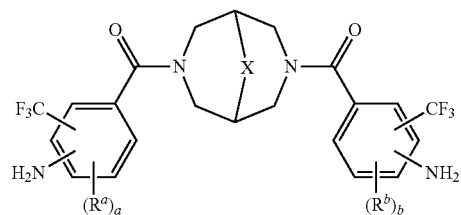

wherein

X is —O— or —S—;

$R^a$ and $R^b$ are independently of each other halogen, C1-C5 alkyl, or haloC1-C5 alkyl;

a and b are independently of each other an integer of 0 or 1; and c and d are independently of each other an integer of 1 or 2.

5. The diamine compound of claim 4, wherein the diamine compound is selected from the following:

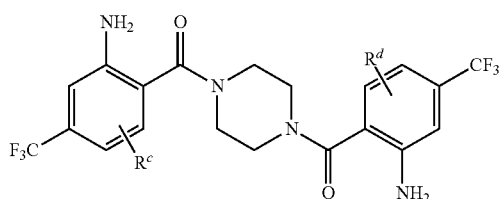

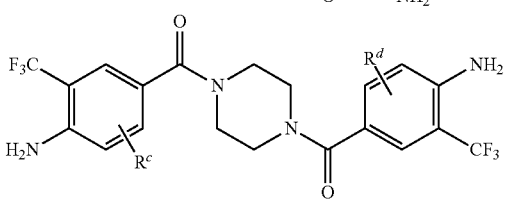

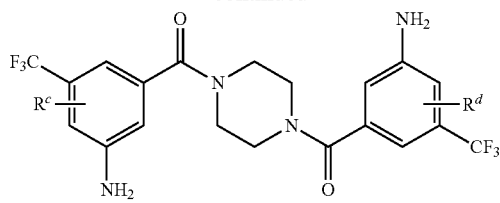

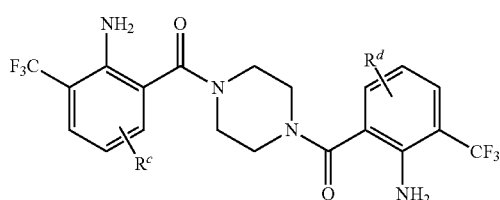

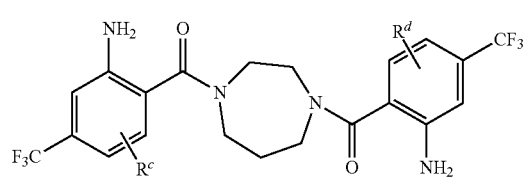

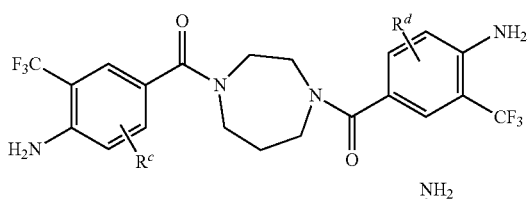

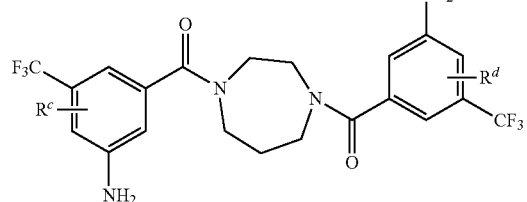

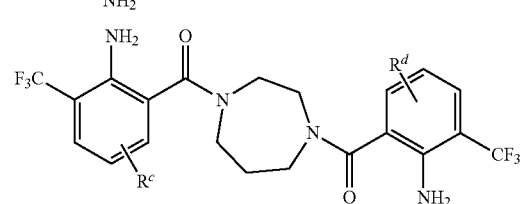

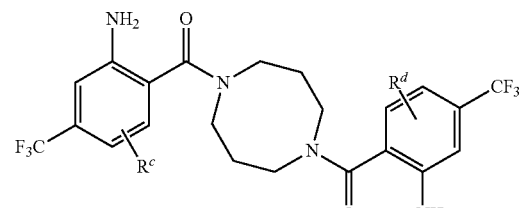

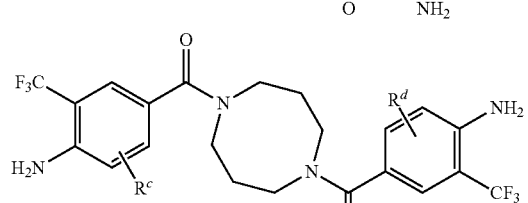

-continued

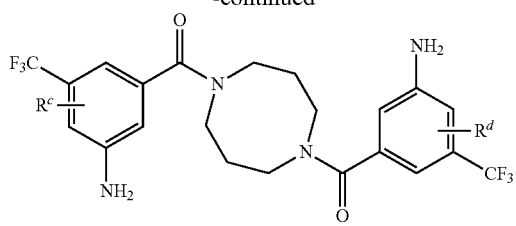

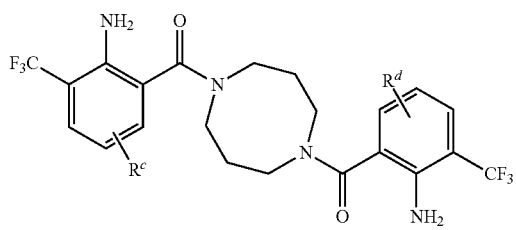

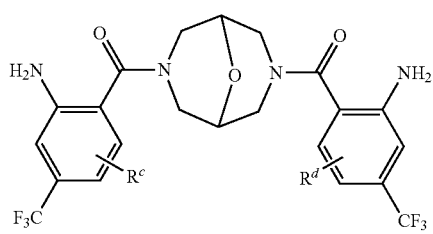

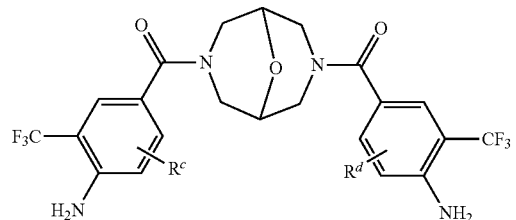

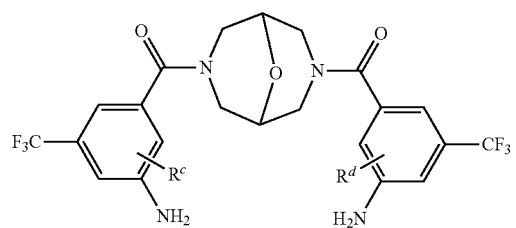

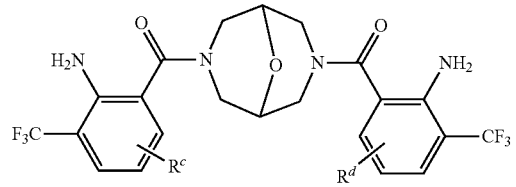

wherein $R^c$ and $R^d$ are independently of each other hydrogen, fluoro, or trifluoromethyl.

6. The diamine compound of claim 1, wherein the diamine compound is used for synthesizing a polyimide-based polymer.

7. A method of preparing the diamine compound of claim 1, the method comprising the steps of:
reacting compounds represented by the following Chemical Formulae B-1 and B-2 with a compound of the following Chemical Formula C to prepare a dinitro compound of the following Chemical Formula A; and
reducing the dinitro compound of Chemical Formula A to prepare a diamine compound represented by the following Chemical Formula 1:

[Chemical Formula 1]

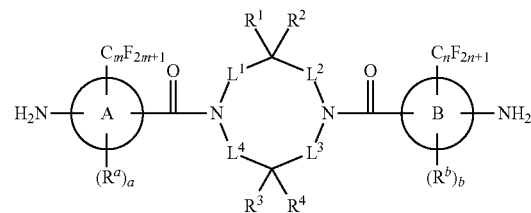

[Chemical Formula A]

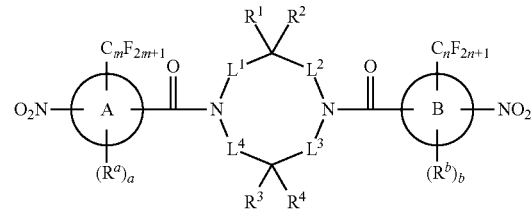

[Chemical Formula B-1]

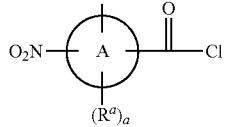

[Chemical Formula B-2]

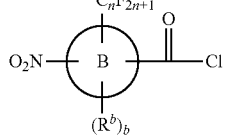

[Chemical Formula C]

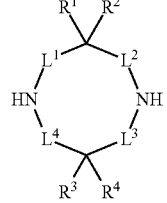

wherein $L^1$ to $L^4$, $R^1$ to $R^4$, ring A, ring B, $R^a$, $R^b$, a, b, m, and n are as defined in claim 1.

8. The method of claim 7, wherein the reducing of the dinitro compound of Chemical Formula A is performed in the presence of hydrogen and one or two or more selected from Pd/C, raney-nickel, Rh/C, Pt/C, and Ru/C, or in the presence of iron and acid.

* * * * *